US006178223B1

(12) United States Patent
Solomon et al.

(10) Patent No.: US 6,178,223 B1
(45) Date of Patent: Jan. 23, 2001

(54) IMAGE RECONSTRUCTION METHOD AND APPARATUS

(75) Inventors: Edward G. Solomon, Menlo Park; Robert E. Melen, Saratoga; Augustus P. Lowell, Sunnyvale; Robert E. Alvarez; Daniel J. Rachlin, both of Mountain View, all of CA (US)

(73) Assignee: Cardiac Mariners, Inc., Los Gatos, CA (US)

( * ) Notice: Under 35 U.S.C. 154(b), the term of this patent shall be extended for 0 days.

(21) Appl. No.: 09/167,171

(22) Filed: Oct. 6, 1998

(51) Int. Cl.[7] .............................. G01N 23/04; A61B 6/03
(52) U.S. Cl. .................................. 378/62; 378/8; 378/15; 378/901
(58) Field of Search .............................. 378/4, 8, 15, 19, 378/62, 901; 382/131

(56) References Cited

U.S. PATENT DOCUMENTS

| 2,638,554 | 5/1953 | Bartow et al. ........................ 250/99 |
| 3,499,146 | 3/1970 | Richards ............................. 250/61.5 |
| 3,742,236 | 6/1973 | Richards ............................. 250/321 |
| 3,746,872 | 7/1973 | Ashe et al. ........................... 250/313 |
| 3,778,614 | 12/1973 | Hounsfield ........................... 250/362 |
| 3,809,886 | 5/1974 | Cochran et al. ...................... 250/323 |
| 3,818,220 | 6/1974 | Richards ............................. 250/61.5 |
| 3,873,834 | 3/1975 | Dammann et al. .................... 250/323 |
| 3,944,833 | 3/1976 | Hounsfield ........................... 250/367 |
| 3,973,128 | 8/1976 | LeMay ................................. 250/445 |
| 3,979,594 | 9/1976 | Anger .................................. 250/369 |
| 4,010,370 | 3/1977 | LeMay ................................. 250/366 |
| 4,144,457 | 3/1979 | Albert ................................. 250/445 |
| 4,188,640 | 2/1980 | Dittrich et al. ..................... 358/111 |
| 4,573,179 | 2/1986 | Rutt .................................... 378/10 |
| 4,598,369 | 7/1986 | Wang et al. ......................... 364/414 |
| 4,630,296 | 12/1986 | Haaker et al. ....................... 378/2 |
| 4,674,046 | * 6/1987 | Ozeki et al. . |
| 4,730,350 | 3/1988 | Albert ................................. 378/10 |
| 4,853,540 | 8/1989 | Nakajima ........................... 250/327.2 |
| 4,903,204 | 2/1990 | Dobbins, III ...................... 364/413.24 |
| 5,022,066 | 6/1991 | Haaker et al. ....................... 378/2 |
| 5,259,012 | 11/1993 | Baker et al. ......................... 378/21 |
| 5,467,404 | * 11/1995 | Vuylsteke et al. . |
| 5,644,612 | 7/1997 | Moorman et al. .................. 378/98.2 |
| 5,699,799 | * 12/1997 | Xu et al. . |
| 5,926,568 | * 2/1999 | Chaney et al. . |

FOREIGN PATENT DOCUMENTS

| WO 94/23458 | 10/1994 | (WO) ........................ H01L/31/115 |
| WO 96/25024 | 8/1996 | (WO) ........................ H05J/35/00 |

OTHER PUBLICATIONS

Barrett et al., "The Theory of Image Formation, Detection, and Processing", vol. 2, *Radiological Imaging*, published at least by Dec., 1981, pp. 368–371.
Curry et al., *Christensen's Physics of Diagnostic Radiology*, Fourth Edition, Lea & Febiger, 1990, pp. 1–522.
Digiray, "Digiray's Reverse Geometry X-ray System", *Digiray Marketing Brochure*, at least by Dec. 1992, pp. 1–2.
Gray, "Application of Optical Instrumentation in Medicine VII", Proceedings of the Society of Photo-Optical Instrumentation Engineers, Mar. 25–27, 1979, vol. 173, pp. 88–95.

* cited by examiner

*Primary Examiner*—David V. Bruce
(74) *Attorney, Agent, or Firm*—Lyon & Lyon LLP

(57) ABSTRACT

An image reconstruction system that can generate an accurate image representation of structure and regions within an object is disclosed. An aspect of the invention comprises a processor that is configured to receive x-ray transmissive information for an object to generate image pixel information for a plurality of depths within the object. The display image comprises selected image pixel information corresponding to image pixels at a plurality of depths within the object.

23 Claims, 16 Drawing Sheets

IMAGE RECONSTRUCTION METHOD AND APPARATUS

BACKGROUND

1. Field of the Invention

The invention pertains to the field of diagnostic x-ray imaging, including among other things, techniques for generating images representative of structures within an object.

2. Description of Related Art

Real-time x-ray imaging is increasingly being required by medical procedures as therapeutic technologies advance. For example, many electro-physiologic cardiac procedures, peripheral vascular procedures, PTCA procedures (percutaneous transluminal catheter angioplasty), urological procedures, and orthopedic procedures require the use of real-time x-ray imaging. In addition, modern medical procedures often require the use of instruments, such as catheters, that are inserted into the human body. These medical procedures often require the ability to discern accurately locations of instruments that are inserted within the human body, often in conjunction with an accurate image of the surrounding body through the use of x-ray imaging.

A number of real-time x-ray imaging systems are known. These include fluoroscope-based systems where x-rays are projected into an object to be imaged, and shadows caused by relatively x-ray opaque matter within the object are displayed on a fluoroscope located on the opposite side of the object from the x-ray source. However, such systems have great difficulty forming images that distinguish particular structures or regions within the depth of the object to be imaged (i.e., where the image is "focused" upon particular structures or regions of interest within the object). This is due in part to the geometry of such fluoroscope-based systems, in which the x-ray opaque properties of the entire depth of the object contributes to the final image, regardless of the exact depth of specific x-ray opaque structures/regions within the object.

One approach to generating an image of particular structures or regions within an object is provided by computed tomography ("CT") imaging systems. In operation, CT systems perform multiple x-ray projections or x-ray measurements of the object to be imaged from multiple angles. The data from the multiple projections can be manipulated to construct an image of a particular plane/slice within the object. Multiple image planes/slices can be made a various depths within the object by moving the CT imaging system and the object relative to each other. However, conventional CT systems are not able to generate a focussed image of at particular structure within an object if the structure of interest lies across multiple image planes/slices at various depths within the object.

Another approach to x-ray imaging involves the use of reverse-geometry x-ray imaging systems. In such systems, an x-ray tube is employed in which an electron beam is generated and focussed upon a small spot on a relatively large target assembly, emitting x-ray radiation from that spot. The electron beam is deflected in a scan pattern over the target assembly. A relatively small x-ray detector is placed at a distance from the target assembly of the x-ray tube. The x-ray detector converts x-rays that strike it into an electrical signal indicative of the amount of x-ray flux detected at the detector. One advantage provided by reverse-geometry systems is that the geometry of such systems allows x-rays to be projected at an object from multiple angles without requiring physical relocation of the x-ray tube. However, the particular x-ray detector used in such systems often limits the spatial resolution of such systems, thereby limiting the quality/range of images that can be obtained. Moreover, known reverse-geometry x-ray imaging systems do not have the functionality to generate a focussed image of structures at various depths within an object.

Therefore, it is desired to create an imaging system that can generate an accurate representation of internal structures within an object.

SUMMARY OF THE INVENTIONS

The present invention comprises an x-ray imaging system capable of local focusing to any depth within an object. According to an aspect, the invention comprises a system for generating a volume of data comprising image information for a plurality of depths with an object under investigation, and selecting data from the volume of data to generate a display image. An aspect of the invention is directed to a processor that is configured to receive x-ray transmissive information for an object to generate image pixel information for a plurality of depths within the object. The display image comprises selected image pixel information corresponding to image pixels at a plurality of depths within the object.

Another aspect of the invention comprises articles of manufacture comprising signals in an image reconstruction system, wherein one or more first signals comprises x-ray transmissiveness information for an object to be imaged, one or more second signals comprises image pixel (or image voxel) information for a plurality of depths within the object, and one or more third signals comprises a display image having data selected from the image pixel information corresponding to a plurality of depths with the object at various depths within the object.

These and other objects, advantages and of aspects of the present invention will become apparent to those of ordinary skill in the art from a consideration of the drawings, description, and claims of the invention contained herein.

DETAILED DESCRIPTION

System Overview

Figure 1:
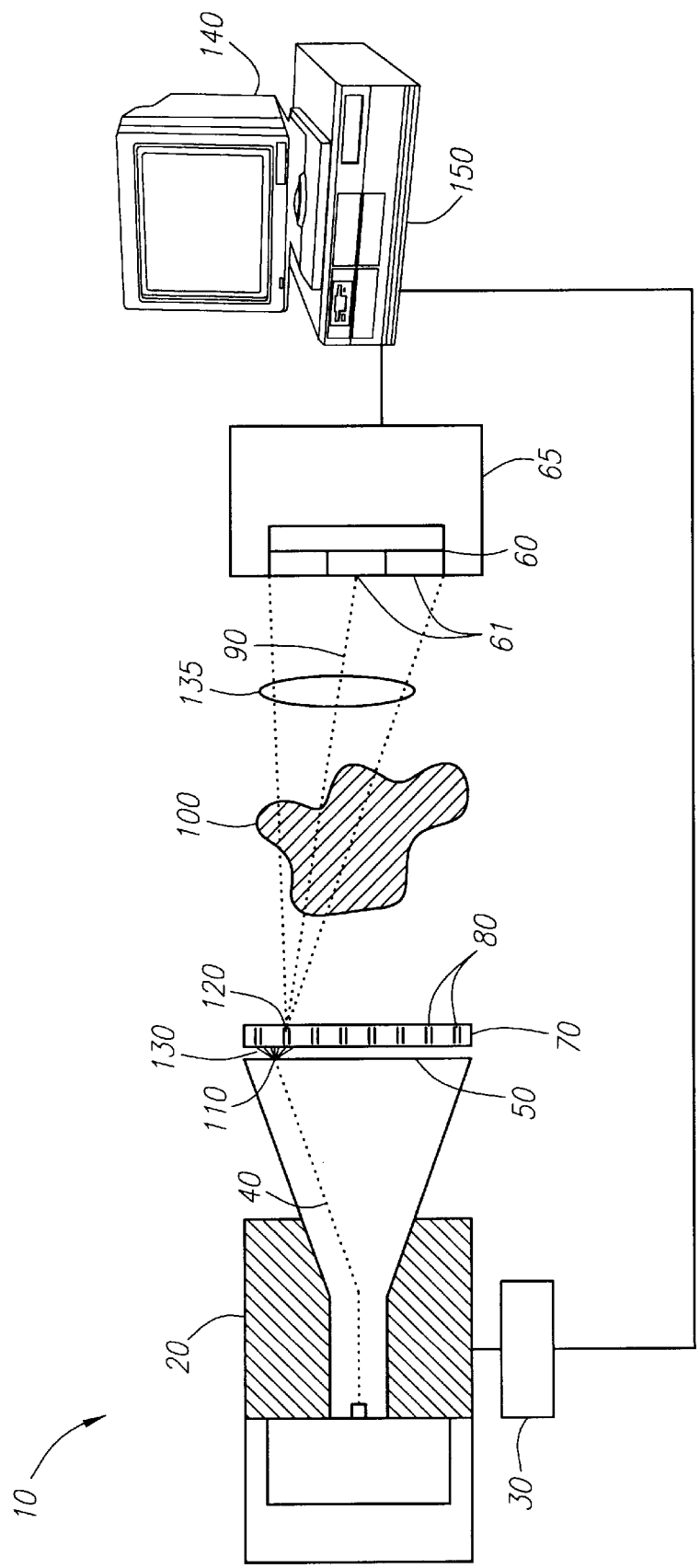
FIG. 1 is a diagram showing components of an x-ray imaging system according to the present inventions.

FIG. 1 is a diagram showing the high level components of an embodiment of a x-ray imaging system according to the invention. X-ray source 10 includes an electron beam source comprising a power supply which can operate x-ray source 10 at about −70 kV to −120 kV. In the present embodiment, this voltage level produces a spectrum of x-rays ranging to 120 keV. Electron beam 40, which is generated within x-ray source 10 by a charged particle gun, is deflected over the surface of a target assembly 50 (which is a grounded anode in an embodiment of the invention) in a predetermined pattern, e.g., a scanning or stepping pattern. X-ray source 10 includes a mechanism to control the movement of electron beam 40 across target assembly 50, such as a deflection yoke 20 under the control of an electron beam pattern generator 30. One advantage provided by the geometry of x-ray source 10 is that it allows x-rays to be projected at an object 100 from multiple angles without requiring physical relocation of the x-ray source 10.

A preferred x-ray source 10 is disclosed in copending U.S. patent application Ser. Nos. 09/167,524 and 09/167,399 No. 237/035) and a preferred target assembly 50 is disclosed in copending U.S. patent application Ser. No. 09/167,523, now U.S. Pat. No. 6,118,853, all filed concurrently with the present application, all of which are incorporated by reference in their entirety. A method and apparatus for generating and moving electron beam 40 across target assembly 50 is disclosed in commonly owned U.S. Pat. No. 5,644,612 which is incorporated herein by reference in its entirety.

In FIG. 1, a collimating assembly is located between target assembly 50 of x-ray source 10 and a multi-detector array 60. In the preferred embodiment, the collimating assembly is located between target assembly 50 and the object 100 for which an image is to be obtained. The presently preferred collimating assembly is collimator grid 70, containing a plurality of x-ray transmissive apertures 80 arranged in a grid pattern. Collimator grid 70 is designed to permit passage of x-rays forming a diverging beam 135 that directly intercepts multi-detector array 60. In an embodiment, collimator grid 70 utilizes a cooling assembly and beam hardening filters. Examples of preferred collimator grids and beam hardening filters that can be utilized in the invention include these depicted and disclosed in copending U.S. patent application Serial No. [Not Yet Assigned] (attorney docket no. 219/160), and U.S. patent application Ser. No. 09/167,639 filed concurrently with the present application, both of which are hereby incorporated by reference in their entirety.

In operation, electron beam 40 preferably dwells at location 110 on target assembly 50 which is located substantially at a position where the axis 90 for a particular aperture 120 of collimator grid 70 intersects the target assembly 50. As the electron beam 40 strikes target assembly 50 at location 110, a cascade of x-rays 130 is emitted. Only the portion of the cascade of x-rays 130 whose path lies substantially along axis 90 pass through aperture 120 and form a diverging x-ray beam 135. The shape of x-ray beam 135 is influenced by the shape of aperture 120. For instance, if the aperture is square the x-ray beam 135 takes on a generally truncated pyramidal shape. If the aperture is circular, x-ray beam 135 takes on a generally conical shape. In a preferred embodiment, the shape and area of the aperture is such that the area of maximum divergence of the x-ray beam 135 is substantially the same as the dimensions of the x-ray capture surface for multi-detector array 60.

Multi-detector array 60 comprises a plurality of discrete detectors (referred to herein as "detector elements") 61 arranged in an array. Each detector element 61 includes a x-ray surface having a capture area for detecting x-rays. Each detector element is capable of independently measuring the amount of x-rays that strike it. When an object 100 is interposed between the x-ray source 10 and the multi-detector array 60, some of the x-rays in x-ray beam 135 will pass through a portion of object 100, and if not scattered or absorbed, will strike the detector elements that make up multi-detector array 60. The x-rays that strike any individual detector element comprise a portion of x-ray beam 135 that is referred to herein as an x-ray beam subpath.

In a preferred embodiment, each detector element comprises components for measuring the quantity of x-ray photons that strike the detector element and outputting a signal representative of that measurement. Alternatively, each detector element includes components for generating an electrical signal generally proportional to the total energy of the x-rays that strike the detector element. The magnitude of the generated electrical signals corresponds to the flux intensity of the x-rays from the appropriate x-ray beam subpath of x-ray beam 135. Utilizing a multi-detector array 60 that independently measures the x-rays which strike each detector element results in the generation of x-ray transmissiveness information that is proportional to the x-ray flux passing through object 100 alone particular x-ray beam subpaths. The resulting intensity data can be used or manipulated to create a representation of object 100, i.e. a representation of the x-ray transmissiveness of object 100, which can be displayed on monitor 140. The presently preferred detector array is disclosed and described in corresponding U.S. application Ser. No. 09/167,397 and U.S. application Ser. No. 09/167,318 filed concurrently herewith, both of which are incorporated by reference in their entirety.

In one embodiment, the number of apertures 80 in collimator grid 70 corresponds to the number of image pixels that are to be displayed on monitor 140 or other visual di splay devices that can be connected to the video output of the x-ray imaging system. Alternatively, the image pixel to aperture ratio is increased, so that the number of apertures are less than the number of image pixels that are displayed on a display device. An "object pixel," for purposes of this discussion, is an area in a plane of the object about which information is being collected. An image pixel is a picture element that is an image representation of one or more object pixels. The presently preferred number of apertures is 10,000 arranged in a 100 by 100 grid. The number of apertures suggested above is for illustrative purpose only and depends on the particular application to which the invention is directed.

X-ray transmissiveness information obtained from the detector elements 61 pertinent to specific image pixels are reconstructed by image reconstruction system 65, as will be described in further detail below. In an embodiment, image reconstruction system 65 also performs control functions and display preparation for the x-ray imaging system. Operational instructions and control of the x-ray source 10, detector 60 and image reconstruction system 65 are made through a control workstation 150. Control workstation 150 also receives operational and status information from the various components of the x-ray imaging system.

For certain applications it may be desirable or necessary to utilize more x-ray flux for each area of object 100 than can be obtained from a single emission from a single aperture. This may occur, for example, if the target assembly material is unable to withstand sufficient electron beam bombardment at one emission (e.g., because of heat generated by the bombardment) necessary to generate the desired amount of x-ray flux. In these applications, multiple smaller x-ray emissions from a single aperture can be performed. The additional x-ray flux can create a potentially more accurate image by decreasing quantum noise. The preferred methods and patterns of stepping electron beam 40 across target assembly 50 is described more fully in copending Patent Application Serial No. [Not Yet Assigned] (Attorney Docket No. 221/261) and patent application Ser. No. 09/1676,397, both filed concurrently with this patent application, both of which are incorporated herein by reference in their entirety.

In many reverse-geometry x-ray systems, the spatial resolution of the resulting image is in large part determined by the capture area of a single detector. Generally speaking, a non-segmented detector with a small capture area can provide high spatial resolution and poor collection efficiency (i.e., the ratio of the meaningful photons passing through the object to the total number of photons passing through the object), while a non-segmented detector with a large capture area provides high collection efficiency and poor spatial resolution. To address this problem, the present invention utilizes a multi-detector array having a relatively large capture area that comprises a plurality of individual detectors with each detector having a relatively small capture area.

Image Reconstruction

Figure 2:
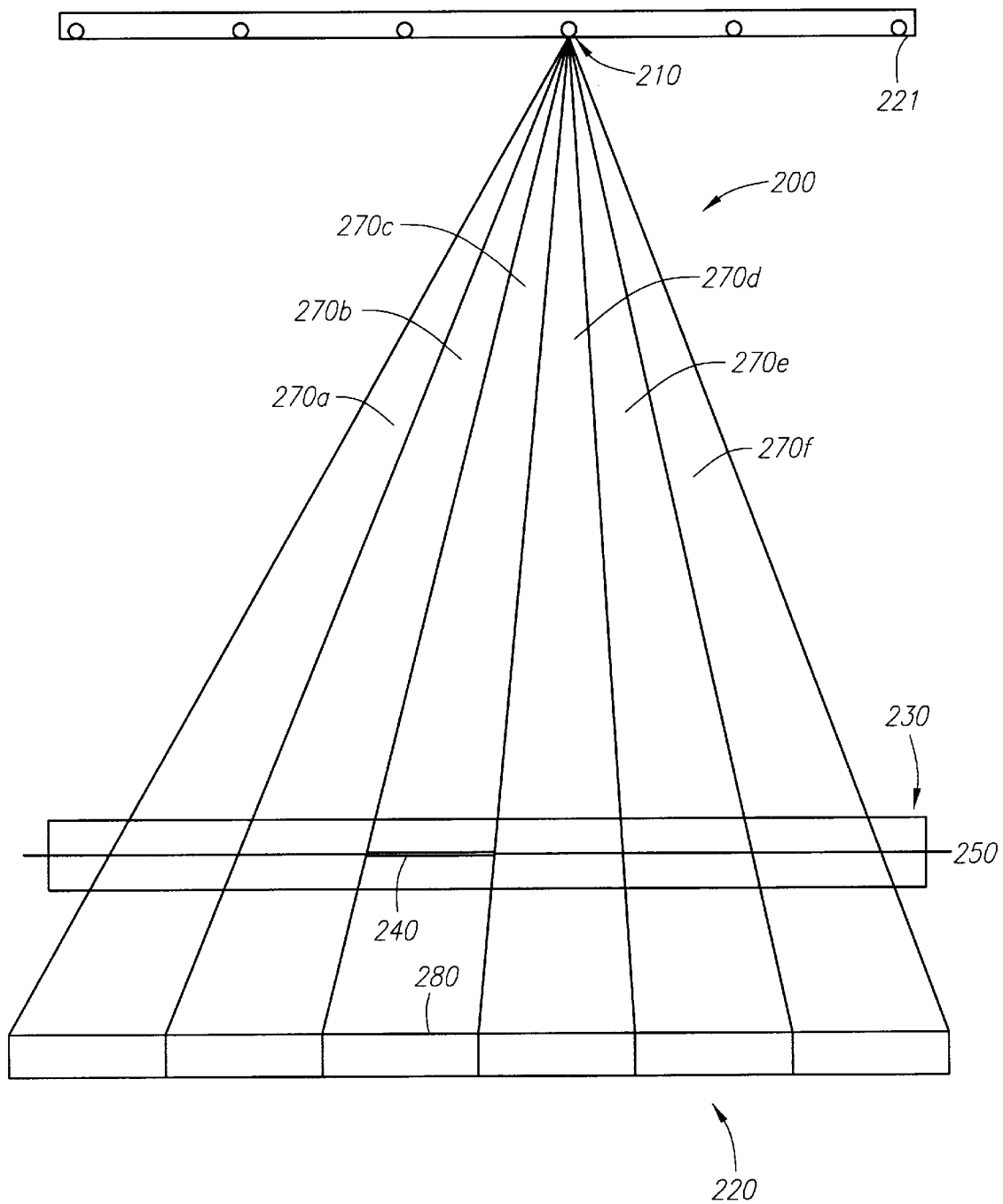
FIG. 2 depicts an x-ray path emanating from a single aperture in a collimator grid and passing through an object on its way to a detector array.

Referring to FIG. 2, a diverging x-ray beam path 200 is depicted emanating from an aperture 210 of a collimator grid 221 and extending to a multi-detector array 220. The x-ray beam path 200 passes through an object 230 on its way to the multidetector array 220. The x-ray beam path 200 intersects object 230 at various planes of interest, such as object plane 250.

X-rays traveling along x-ray beam path 200 diverge after exiting aperture 210, preferably having a cross sectional area varying from a minimum area approximately equal to the size of the aperture up to a maximum area approximately equal to an area covering the detection surface of multi-detector array 220. In an embodiment, multi-detector array 220 is positioned such that the maximum surface area of x-ray beam path 200 only covers the total capture area of the multi-detector array 220 without extending beyond this area. This minimizes the generation of x-rays that provide no meaningful image information.

X-ray beam subpaths 270a, 270b, 270c, 270d, 270e, and 270f are defined by the capture size and quantity of the various detector elements that comprise multi-detector array 220. The shape of the volume of the x-ray beam subpath is essentially defined by the shape of the detector elements. In other words an x-ray beam subpath (e.g., x-ray beam subpath 270c) is the volume defined by the elongated shape having a truncated apex at an aperture 210 and a base having an area of the capture area of a detector element 280. If the detector element capture area is round, the shape of an x-ray beam subpath is substantially conical. If the detector element capture-area is square, the shape of an x-ray beam subpath is substantially pyramidal.

Object pixel 240 is an area within plane of interest 250. When a reconstructed image is displayed, object pixel 240 could be represented by a particular image pixel which is constructed using information obtained from certain x-ray beam subpaths that intersect object pixel 240.

Each detector element 280 of multi-detector array 220 detects x-rays that have passed through object 230 for a particular portion of x-ray beam path 200. The quantity of x-rays detected at a detector element 280 provides information about the x-ray transmissiveness for object 230 at a particular object pixel 240. The x-ray beam path 200 from each aperture 210 provides information to create a group of discrete pieces of information concerning the x-ray transmissiveness of the object. The number of discrete pieces of information generated for x-ray beams emanating from a single aperture corresponds to the number of individual detector elements 280 in the multi-detector array 220. The presently preferred detector array is comprised of 48 by 48 detector elements. Thus, for each x-ray beam 200 emanating from an aperture 210, this results in 2,304 discrete pieces of information concerning the x-ray transmissiveness of object pixels for an object plane defined within the object. The x-ray transmissiveness information obtained by the detector elements from each of the x-ray beam subpaths is available for use in generating image pixel information.

Figure 3:
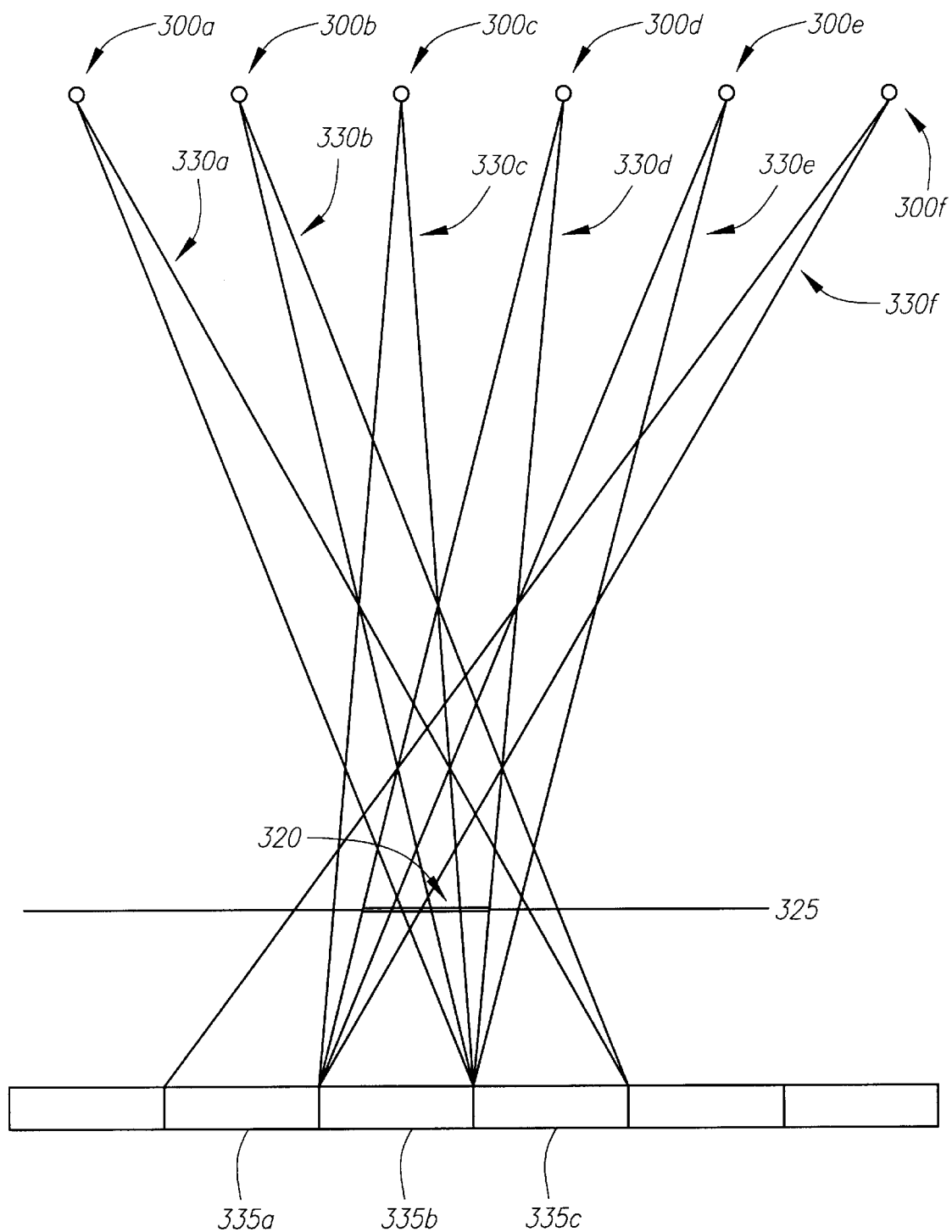
FIG. 3 depicts multiple x-ray beam subpaths emanating from multiple apertures in a collimator grid and passing through an object to a detector array.

Imaging data for object pixels can be generated by collecting x-ray transmissiveness information measured for x-ray beam subpaths that intersect a particular object pixel on a particular plane of interest. Depending on the plane of interest chosen, the intersection of the subpaths on that plane of interest may not be fully coincident but may be only partially coincident. Referring to FIG. 3, shown are x-ray beam subpaths 330a, 330b, 330c, 330d, 330e, and 330f emanating from apertures 300a, 300b, 300c, 300d, 300e and 300f respectively. Each of these x-ray beam subpaths are portions of their respective x-ray beams that are either completely or partially coincident with object pixel 320 on a plane of interest 325. By taking into consideration the x-ray transmissiveness information obtained by the detectors 335a–c for x-ray beam subpaths 330a–f (along with any other x-ray beam subpath-detector combinations that provide relevant information about object pixel 320), image data that accurately represents the x-ray transmissiveness of an object at object pixel 320 can be reconstructed.

Figure 4:
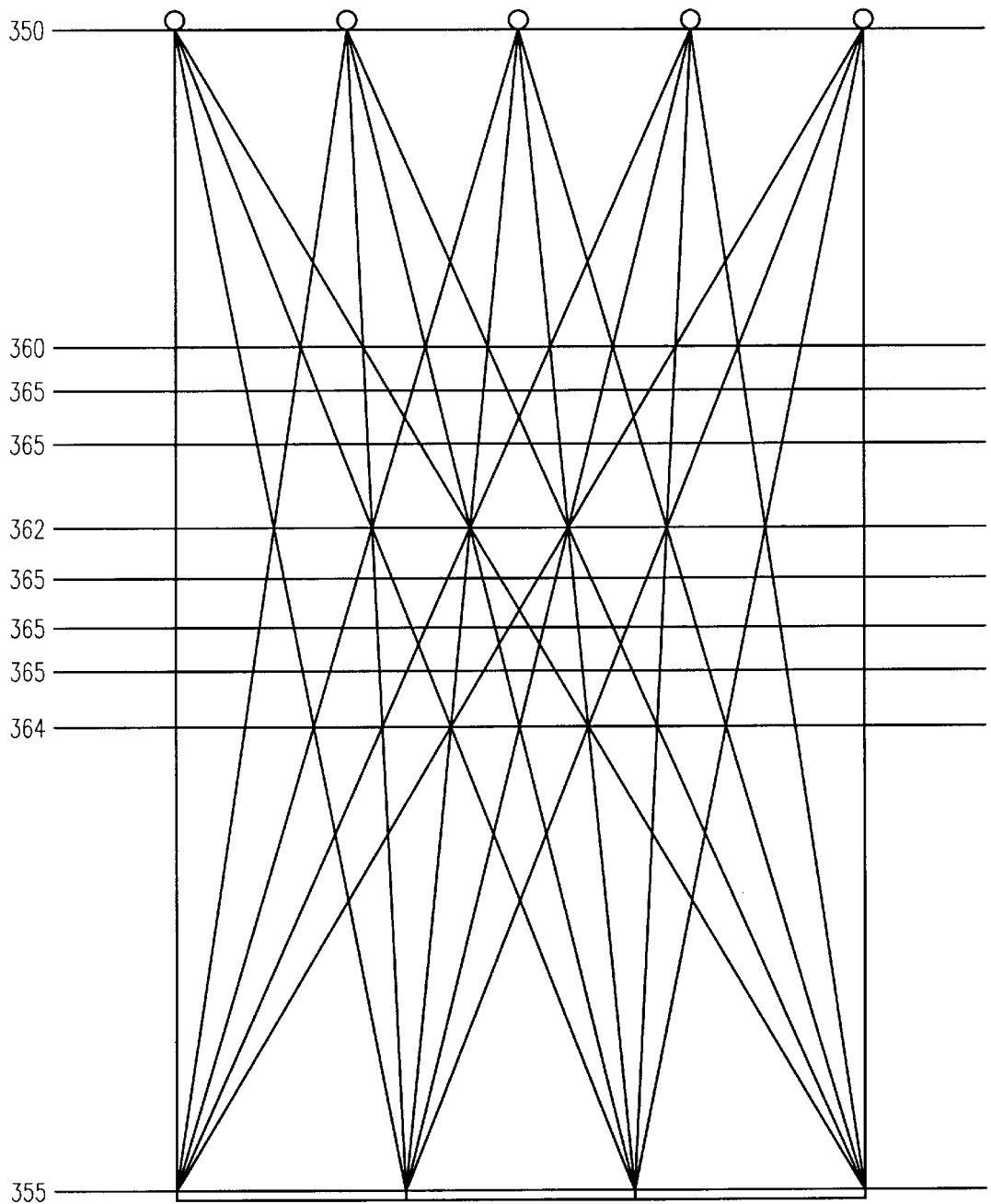
FIG. 4 is a diagram that shows the location of a plurality of planes between a source plane and a detector plane according to one embodiment of the present inventions.

As depicted in FIG. 4, there are numerous planes parallel to the source plane 350 and detector plane 355. Some of the parallel planes are located where multiple x-ray beam subpaths are fully coincident through regularly-spaced areas in the plane. These planes are referred to as focal planes and the regularly spaced areas within the plane can be identified as object pixels. Examples of focal planes in FIG. 4 are planes 360, 362, and 364. Each focal plane comprises characteristics which differ from other focal planes, including distance from the source, pitch of the object pixels, and specific areas of the object that intersects the focal plane. Non-focal planes 365 are located between any two focal planes, and in these non-focal planes, x-ray beam subpaths emanating from the source plane are only partially coincident with each other.

Figure 5:
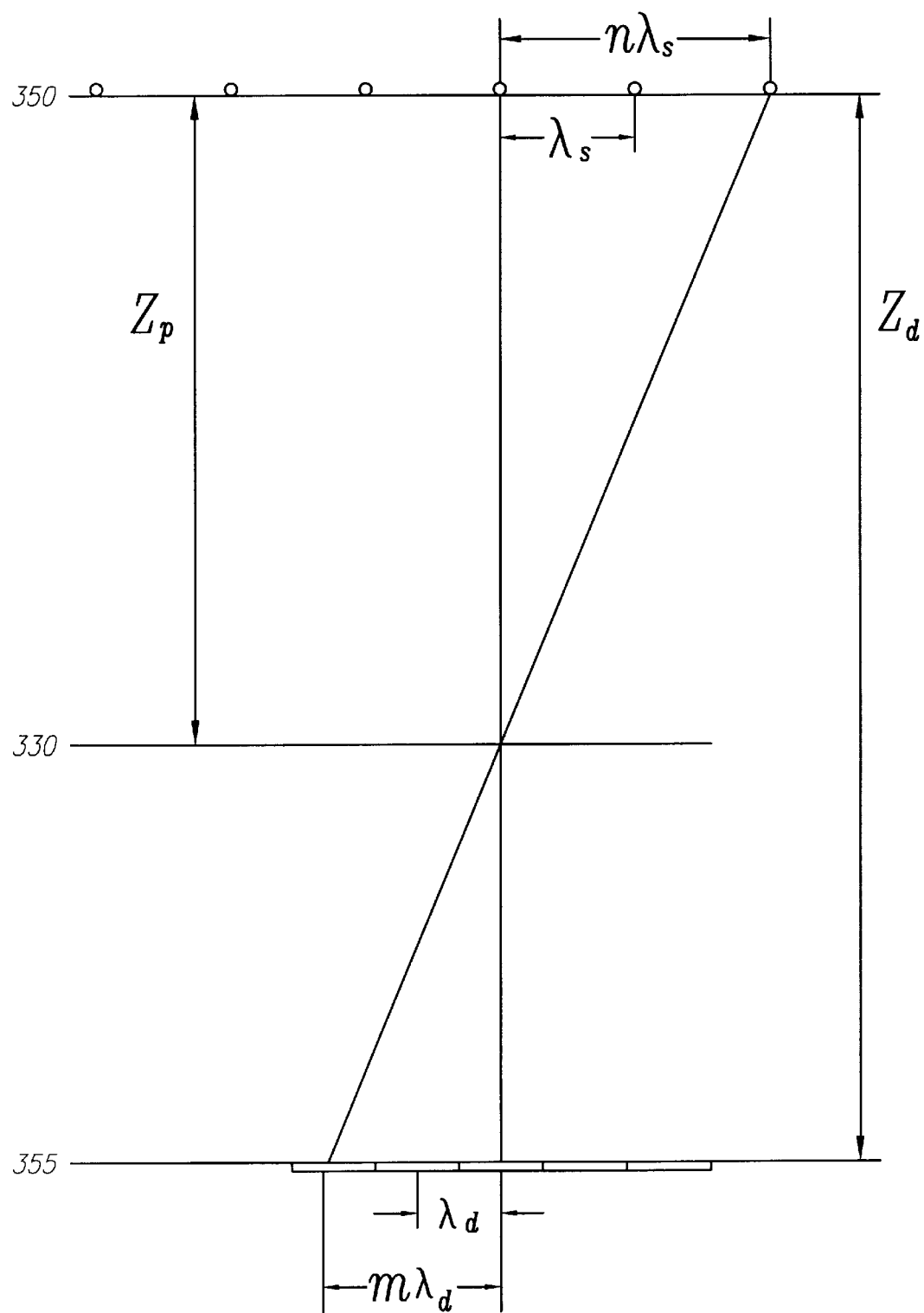
FIG. 5 is a diagram of showing the geometry between an array of regularly-spaced x-ray sources and an array of detectors.

Referring to FIG. 5, a method is provided to reconstruct both focal and non-focal planes as two-dimensional planes of object pixels. Consistent with the invention, an array of x-ray beam source locations, preferably a rectangular array of $SOURCE_x$ by $SOURCE_y$ sources with a pitch $\lambda_s$ in both the x- and y-directions, is used with an array of detectors, preferably a square array of $DET_x$ by $DET_y$ detectors on a pitch $\lambda_d$ in both the x- and y-directions. In an embodiment, each source is a separate aperture within a collimation grid that emanates an x-ray beam path that covers the capture surface of the multi-detector array. Each x-ray beam path is divided into a plurality of x-ray beam subpaths, with the x-rays in each x-ray beam subpath providing intensity data to a single detector element. Thus, there are $DET_x*DET_y$ x-ray beam subpaths per x-ray path and $SOURCE_x*SOURCE_y$ x-ray beam paths for a total of $DET_x*DET_y*SOURCE_x*SOURCE_y$ x-ray beam subpaths from all sources in the array of sources. INTENSITY(i,j,k,l) represents the intensity data for x-rays detected at a detector DET(i,j) from x-rays generated by a SOURCE(k,l).

A focal plane can be described by a pair of natural numbers (integer>1) m and n where $m*\lambda_d$ and $n*\lambda_s$ are the baseline lengths of similar triangles. However, any plane whether focal or non-focal can be reconstructed by use of the present invention. All that is required in order to reconstruct a plane is that the plane being reconstructed be capable of being described by values of m and n which are real numbers greater than zero.

$Z_d$ represents the distance from the source plane 350 to the detector plane 355 while $Z_p$ represents the distance from the source plane 350 to a particular object plane 330. Therefore, the distance $Z_p$ is described by the values of m,n and can be expressed as:

$$Z_p(m, n) = Z_d \frac{n*\lambda_s}{n*\lambda_s + m*\lambda_d} \qquad \text{EQ. 1}$$

According to an embodiment of the invention, reconstruction of a two-dimensional array of image pixels IMAGE (m,n) at an object plane defined by m and n can be performed by creating an array of an image pixel values corresponding to object pixels on the plane. The image pixel values are generated by mathematically manipulating each value of INTENSITY (i, j, k, l) that corresponds to a particular object pixel on the object plane. In an embodiment, the values of INTENSITY (i,j,k,l) for each object pixel are summed to generate the image pixels for an object plane. In the present embodiment, each value of INTENSITY (i,j,k,l) is summed into the appropriate image pixel defined by IMAGE (i*n+k*m, j*n+l*m).

In the case of a non-focal plane, any value which is not a whole number is preferably assigned to the appropriate image pixel based upon the conventional rules of rounding to the whole number. For example, in reconstructing the m=10 and n=1.33 plane, an x-ray beam subpath from a source having the x-y indices (1,1) projecting onto a detector element having the x-y indices (1,2) (which is represented as INTENSITY (1,2,1,1)) corresponds to an object pixel at coordinates (1*1.33+1*10, 2*1.33+1*10) or (11.3, 12.7). This x-ray beam subpath passes through and contains information regarding object pixels at coordinates (11, 12), (12, 12), (11, 13), and (12, 13). Thus, the x-ray transmissiveness value obtained from INTENSITY (1,2, 1,1) could be assigned to any of the image pixels at coordinates (11,12), (12,12), (11,13) and/or (12,13). It is presently preferred that the normal rules of rounding apply and object pixel (11.3, 12.7) is assigned to image pixel (11,13). It should be noted that other methods of assigning x-ray beam subpaths to image pixel coordinates can be employed without departing from the scope of the present invention.

The maximum x- and y-indices of array IMAGE (m,n) can be expressed as $DET_x*n+SOURCE_x*m$ and $DET_y*n+SOURCE_y*m$ respectively. In the present embodiment, multiplying the baselines of the similar triangles, e.g., doubling or tripling them, does not change the position of the resulting plane to be imaged.

The pitch $\lambda_p$ of object pixels in a particular object plane $Z_p$ (m,n) can be expressed as follows:

$$\lambda_p(m, n) = \frac{\lambda_d}{n} * \frac{Z_p(m, n)}{Z_d} \qquad \text{EQ. 2(a)}$$

$$= \frac{\lambda_d}{n} * \frac{n*\lambda_s}{n*\lambda_s + m*\lambda_d} \qquad \text{EQ. 2(b)}$$

$$= \frac{\lambda_d*\lambda_s}{n*\lambda_s + m*\lambda_d} \qquad \text{EQ. 2(c)}$$

In an embodiment, every $m^{th}$ detector in the x- and y-directions provides intensity information for use in reconstructing one or more selected object pixels in an object plane. Therefore, there are approximately $DET_x*DET_y/m^2$ detectors or x-ray beam subpaths that provide intensity information per object pixel. Since the total number of x-ray beam subpaths in the present embodiment is $DET_x*DET_y*SOURCE_x*SOURCE_y$, the number of object pixels in an object plane about which x-ray transmissiveness information can be obtained for use in reconstructing an image can be expressed as:

$$\frac{DET_x*DET_y*SOURCE_x*SOURCE_y}{DET_x*DET_y/m^2} = \qquad \text{EQ. 3}$$

$$SOURCE_x*SOURCE_y*m^2$$

Due to the fact that the object pixels around the perimeter of the intersection area do not receive complete intensity information (i.e., the number of detector elements measuring the amount of flux passing through these object pixels are less than for other object pixels), the number of object pixels in an object plane providing meaningful intensity information may be slightly lower than the above number.

For example, the n=1.33 and m=10 plane in a system with a 100×100 array of sources has 1,000,000 (100×100×10²) object pixels in any object plane. Furthermore, the m=10 and n=1.33 plane has 23,040,000 (48×48×100×100) x-ray beam subpaths if a 48×48 array of detector elements is used. In this example, there should be approximately 23 x-ray beam subpaths which are completely or partially coincident to each object pixel. However, due to the geometry of the system, object pixels on the edge of the object plane may have less than 23 x-ray beam subpaths which are completely or partially coincident to them.

When the size of the source array is $SOURCE_x* \lambda_s$ by $SOURCE_y* \lambda_s$, the size of the field of view at a particular object plane can be expressed as:

$$SOURCE_x*\lambda_s*\left(1 - \frac{Z_p}{Z_d}\right) \text{by } SOURCE_y*\lambda_s*\left(1 - \frac{Z_p}{Z_d}\right) \qquad \text{EQ. 4}$$

The field of view can be changed by using some as opposed to all of the sources of the source array. By using a smaller number of apertures located in a certain area of the collimator grid, the area to be imaged can be made smaller.

In constructing each image plane, the x-ray transmissiveness information should be processed such that it is always associated with the image pixel to which it has been assigned. In addition, if the preferred stepping pattern of the electron beam is utilized, each aperture will emit x-rays more than one time for the creation of a single frame and each detector element will provide x-ray transmissiveness information assigned to the same image pixel more than once. In this situation, it is presently preferred that x-ray transmissiveness information obtained from the same detector element from x-rays emanating from the same aperture in the same frame is combined together prior to combination with other x-ray transmissiveness information assigned to the same image pixels that resulted from x-rays that emanated from other apertures in that frame.

The present invention takes into account that it is not really a two-dimensional plane which is constructed by mathematically combining related x-ray beam subpaths, but a volume slice having some depth. X-ray absorbency, measured as x-ray intensity by the detector elements, is a measure according to depth. Without measuring x-ray absorbency over a depth, there would be little or no contrast between object regions of different density. Thus, a reconstructed image array represents a two dimensional object plane within a reconstructed "slice". A slice is a substantially planar region within the object having some depth. The term "voxel" refers to a volume element located within a slice of the object to be imaged.

The image reconstruction method of the present invention generates information for a wide variety of planes and slices at numerous positions between the source and detector planes. The ability to reconstruct a wide variety of planes/slices is used to generate images of particular areas of the object by selecting a suitable slice near the region of interest of the object, without having to change the respective positions of the source and detector.

The image reconstruction method also increases the effective depth of field of a generated image by providing the capability to reconstruct multiple planes/slices in a region of interest. The image planes, which represent reconstructed slices, can be combined to produce a single array of image pixels with high spatial resolution in the area of interest.

Figure 6:
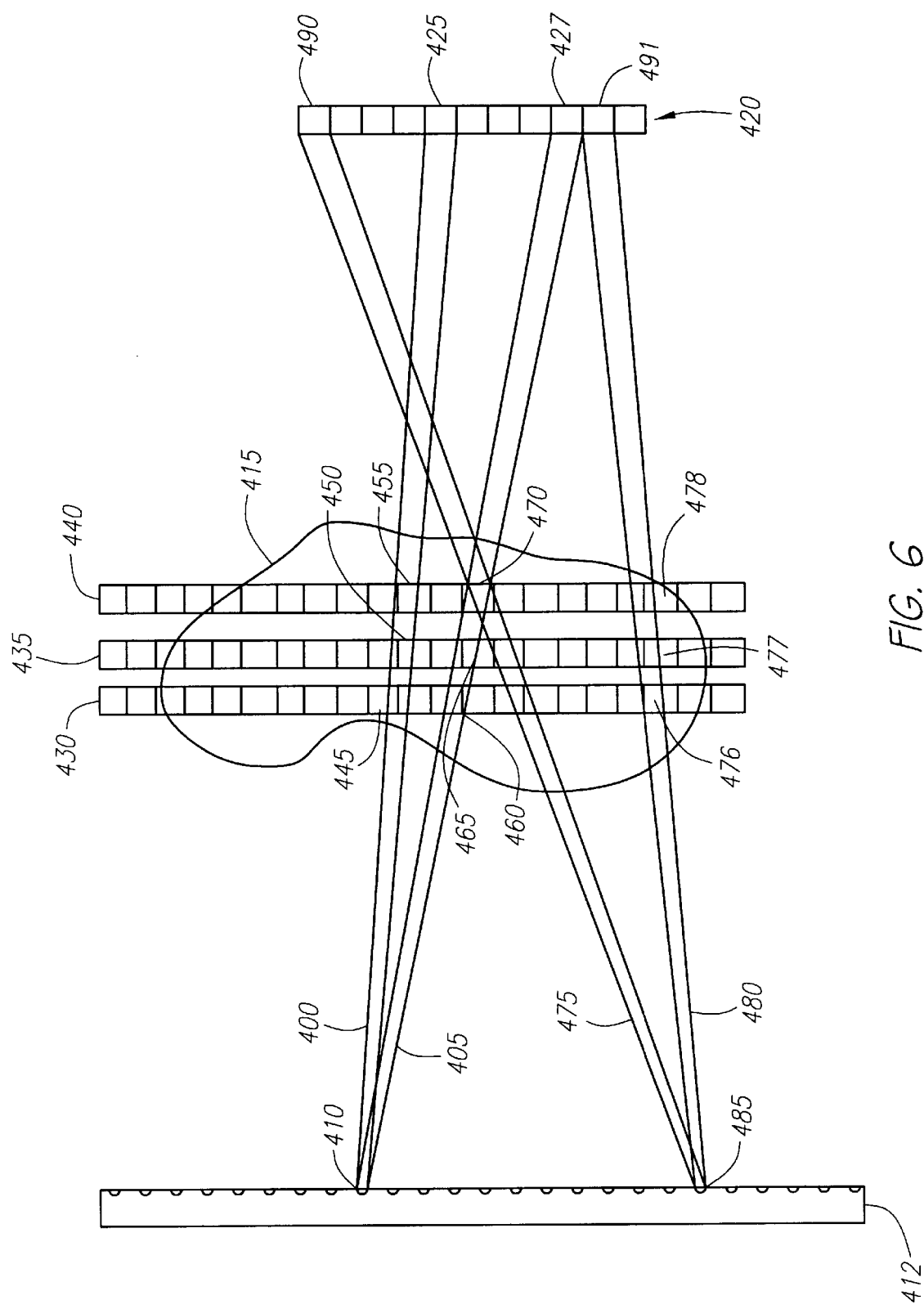
FIG. 6 is a diagram illustrating x-ray beam subpaths through an object to a detector array.

Referring to FIG. 6, a first x-ray beam subpath 400 and second x-ray beam subpath 405 are M o of many x-ray beam subpaths emanating from a first aperture 410 of collimation grid 412. The remaining x-ray beam subpaths are not shown for the sake of clarity and explanation. Some of the x-rays that travel along first x-ray beam subpath 400 and second x-ray beam subpath 405 pass through object 415 and strike detectors 425 and 427, respectively, of multi-detector array 420. The information provided to detector 425 by x-rays traveling along first x-ray beam subpath 400 does not correspond to any single point within object 415, rather the path of the first x-ran beam subpath 400 as it passes through the object 415 forms a volume which intersects first slice 430, second slice 435, and third slice 440. Particularly, x-rays traveling along first x-ray beam subpath 400 creates a volume which is completely or partially coincident with first voxel 445, second voxel 450, and third voxel 455. For the purposes of reconstruction, the information obtained by detector 425 from x-ray beam subpath 400 can be used to generate an image pixel representing first voxel 445 in an image plane representing slice 430, can be used to generate an image pixel representing second voxel 450 in an image plane representing slice 435, and/or can be used to generate an image pixel representing third voxel 455 in an image plane representing slice 440. From this data, image planes are created using the methods described with respect to FIGS. 2–6.

With respect to second x-ray beam subpath 405, the information provided by detector 427 can be used to generate an image pixel representing fourth voxel 460 in an image plane representing slice 430, can be used to generate an image pixel representing fifth voxel 465 in an image plane representing slice 435, and/or can be used to generate an image pixel representing sixth voxel 470 in an image plane representing slice 440.

A third x-ray beam subpath 475 and fourth x-ray beam subpath 480 are two of many x-ray beam subpaths emanating from a second aperture 485. The remaining x-ray beam subpaths emanating from second aperture 485 are not shown for the sake of clarity and explanation. Some of the x-rays that travel along x-ray beam subpath 475 and x-ray beam subpath 480 pass through object 415 and strike detectors 490 and 491, respectively. The intensity information provided to detector 490 by x-rays traveling along third x-ray beam subpath 480 does not correspond to any single point within object 415, rather the intensity information is an aggregation of information for a volume that insects all plane/slices between collimation grid 412 and multi-detector array 420, including the planes/slices containing voxels 476, 477, and 478.

In an embodiment, an image pixel is created by combining or summing the intensity for a voxel from all of the detectors that detect x-rays traveling along x-ray beam subpaths that are completely or partially coincident with that particular voxel and have been assigned to that voxel for the purpose of reconstruction. For example, an image pixel representing sixth voxel 470 would include intensity data collected by detector 427 from x-ray beam subpaths 405 and intensity data collected by detector 490 from x-ray beam subpath 475.

The preferred reconstruction method individually reconstructs a number of slices simultaneously. In the example of FIG. 6, slices 430, 435 and 440 are reconstructed individually, and the various image pixels/voxels that make up each slice are combined or otherwise manipulated to create an array of display pixels for producing an image on a display monitor or film.

The image pixels of the reconstructed slices, can be stored in a memory as image planes, and can be used to display an image on a two dimensional display. A two dimensional display is composed of the array of display pixels that each represent a position on the display. The display pixels have only two dimensions, x and y, whereas the image pixels have not only x and y coordinates but also a z coordinate corresponding to the distance of the image pixel from the source (or detector). For example, the image pixels in the slice closest to the source can be assigned a z value of 1 and the image pixels in the image slice farthest from the source can be assigned a z value of p, where p is the total number of image slices created.

If an image on a two dimensional display is created by combining all the image planes/slices together, the display pixels may appear as an image with indistinct edges. This is because the image displayed may not correspond to only one or two image pixels but to all of the image pixels that have the same x and y coordinates on differing image planes/slices. In order to view meaningful images, preferably only one image pixel out of a number of image pixels having a different z coordinates but having the same x and y coordinates is selected for display as a display pixel. A display image is formed from a set of these selected image pixels corresponding to particular x,y coordinates on a display device. Note that when using the invention, the display image can focus upon more than one region or structure of interest at multiple depths within an object that is being imaged.

Alternatively, it is possible to form part of the display image by combining one or more image pixels having the same x and y coordinates from different image planes/slices. The combined intensity data for the image pixels having the same x and y coordinates but different z coordinates can be displayed as a single display pixel with the appropriate x-y coordinates. Combining image pixels from two or more planes/slices can be performed if relevant information about the object(s) under investigation is located on multiple image planes/slices, and if it is more appropriate to form a display pixel representing the multiple sets of information than it is to select only one of the image pixels for display.

There are a number of methods that can be used to select which of the image pixels that have the same x and y coordinates but different z coordinates corresponding to different image planes/slices to display. A currently preferred method for selection is a maximum intensity projection algorithm. For each set of image pixels which have the same x and y coordinates but a different z coordinate, the maximum x-ray intensity projection algorithm selects the image pixel that has the greatest intensity value from the set. This image pixel which has the maximum x-ray intensity or luminance value is then displayed on the display as a display pixel having the appropriate x and y coordinates.

An alternative algorithm is a minimum intensity projection algorithm that selects for display the image pixel of the set of image pixels having the same x and y coordinates but different z coordinates that has the lowest intensity or luminance value.

Another method for selecting which of the image pixels that have the same x and y coordinates but different z coordinates corresponding to different image planes/slices to display involves selection of a portion of a plane/slice which has the greatest contrast in a particular region in order to display an object in the field of view.

Another method for selecting which of the image pixels that have the same x and y coordinates but different z coordinates corresponding to different image planes/slices to display involves selection of a portion of a plane/slice which has the greatest energy within a particular spatial frequency range in a particular region in order to display an object in a field of view.

Yet another method for selecting which of the image pixel that have the same x and y coordinates but different z coordinates corresponding to different image planes/slices to display involves selection of a portion of a plane/slice which has the greatest detail in a particular region in order to display an object in the field of view. In an embodiment of this approach, for each image pixel ($I_{x,y}$), two of the nearest neighbors are used to determine the slope as follows:

$$\text{Slope} = \sqrt{(I_{x,y} - I_{x+1,y})^2 + (I_{x,y} - I_{x,y+1})^2} \qquad \text{EQ. 5}$$

An alternate slope or gradient determination can be performed in which the absolute value of the difference of adjacent or otherwise neighboring pixels are calculated to determine the slope. For example, the following equation can be used to determine the slope:

$$\text{Slope} = |I_{x,y} - I_{x+1,y}| + |I_{x,y} - I_{x,y+1}| \qquad \text{EQ. 6}$$

The image pixel ($I_{x,y}$) that has the largest slope of the group having the same x,y but different z coordinates is then chosen for display. Other slope calculations may be utilized within the scope of the invention, including taking into account image pixels within the same vicinity or other methods of calculating, including weighting the image pixel slope values depending on the positioning of the image pixels.

In an alternative embodiment, it is possible that a display is created by selecting all of the image pixels from a single image plane for display. In an embodiment, the single plane selected is the one which has the greatest contrast within the plane as a whole.

It is further possible to combine any two or more of the disclosed methods depending upon the needs of the particular use or application.

Note that the foregoing methods for selecting which of the image pixels that have the same x and y coordinates but different z coordinates corresponding to different image planes/slices to display can be equally applied to other imaging modalities that reconstruct planes/slices (or other types of imaging data) at various depths within an object. For example, the methods can be applied to multi-slice CT data to display an image of an object in the field of view.

Image Reconstruction System

Figure 7:
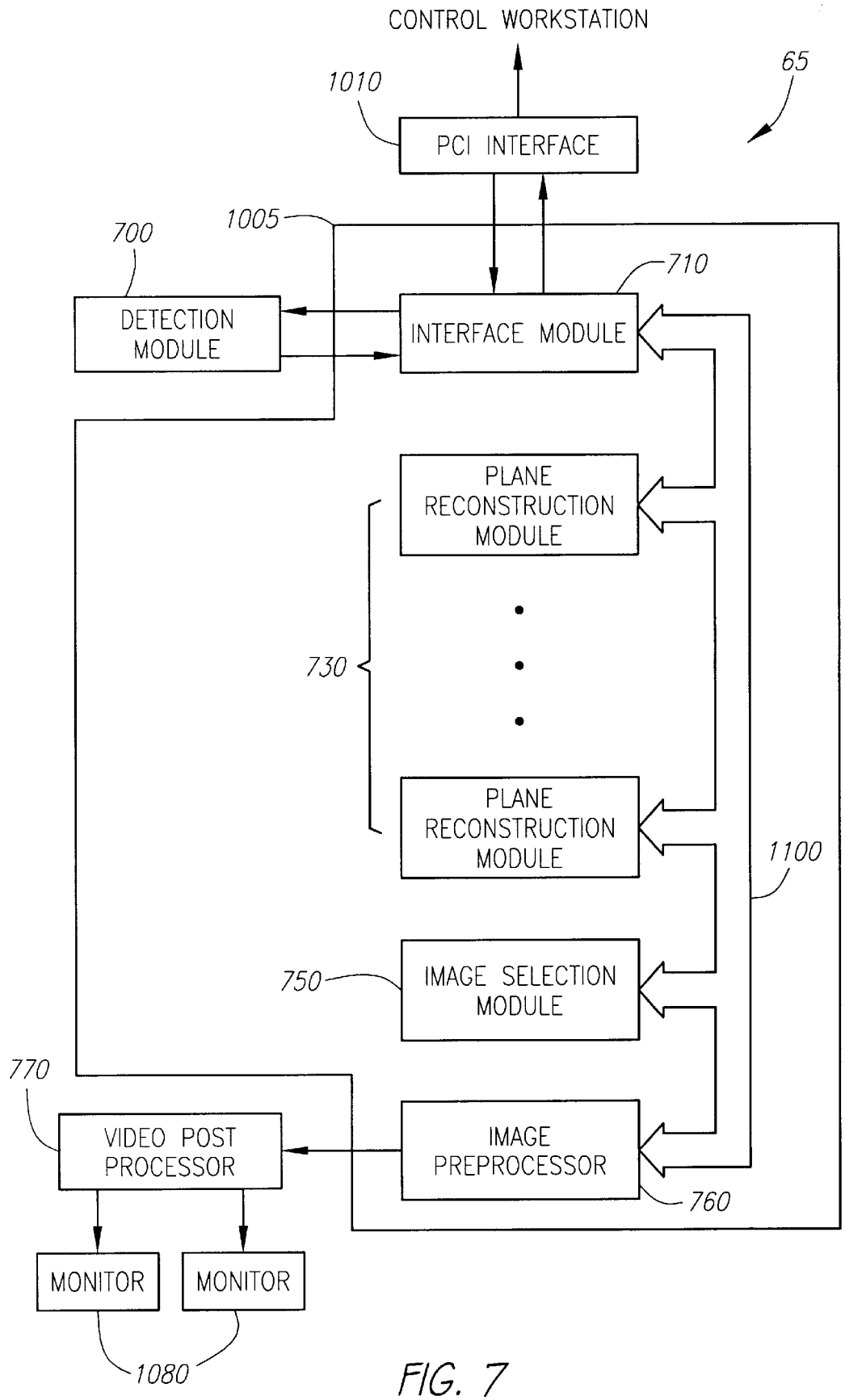
FIG. 7 is a block diagram of an embodiment of an image reconstruction system according to the present inventions.

FIG. 7 depicts a block diagram of an embodiment of image reconstruction system 65. The image reconstruction system 65 comprises a PCI interface 1010 which connects to a control workstation 150. In an embodiment, a detection module 700 comprises the components of multi-detector array 60 and receives x-ray transmissiveness information. Alternatively, multi-detector array 60 is physically separate from the image reconstruction system 65 and the detection module 700 comprises components to receive data signals from the multi-detector array 60. Image reconstruction chassis 1005 comprises an interface module 710, one or more plane reconstruction modules 730, an image selection module 750 and an image preprocessor 760. The various components on the image reconstruction chassis 1005 are interconnected via one or more busses 1100, which also include control lines. Video post processor 770 is coupled to display monitors 1080. In an embodiment, each of the above components can be implemented utilizing Field Programmable Gate Arrays, however any circuitry, chip or hardware/software combination which can implement the described functions can be used without departing from the scope of the present inventions.

Detection module 700 can operate in a number of modes which effect whether and how the detection module combines the x-ray transmissiveness information obtained from the multi-detector array 60 and when the x-ray transmissiveness information is output to interface module 710. The modes include: (1) An image acquisition mode in which the x-ray transmissiveness information detected at the detector array are output to interface module 710 for image processing; (2) A sensor mode where the x-ray transmissiveness information is input for diagnostic purposes; (3) An alignment mode where the x-ray transmissiveness information obtained by the multi-detector 60 is used to align the electron beam position on the target assembly with the apertures of the collimator grid; and (4) An image test mode where x-ray transmissiveness information is combined in the same way as in image acquisition mode, but the x-ray transmissiveness information is transmitted to interface module 710 only in response to a specific timing control signal. More details regarding these imaging modes are described in copending U.S. application Ser. No. 09/167, 397, filed concurrently herewith, which is hereby incorporated by reference in its entirety.

Figure 9:
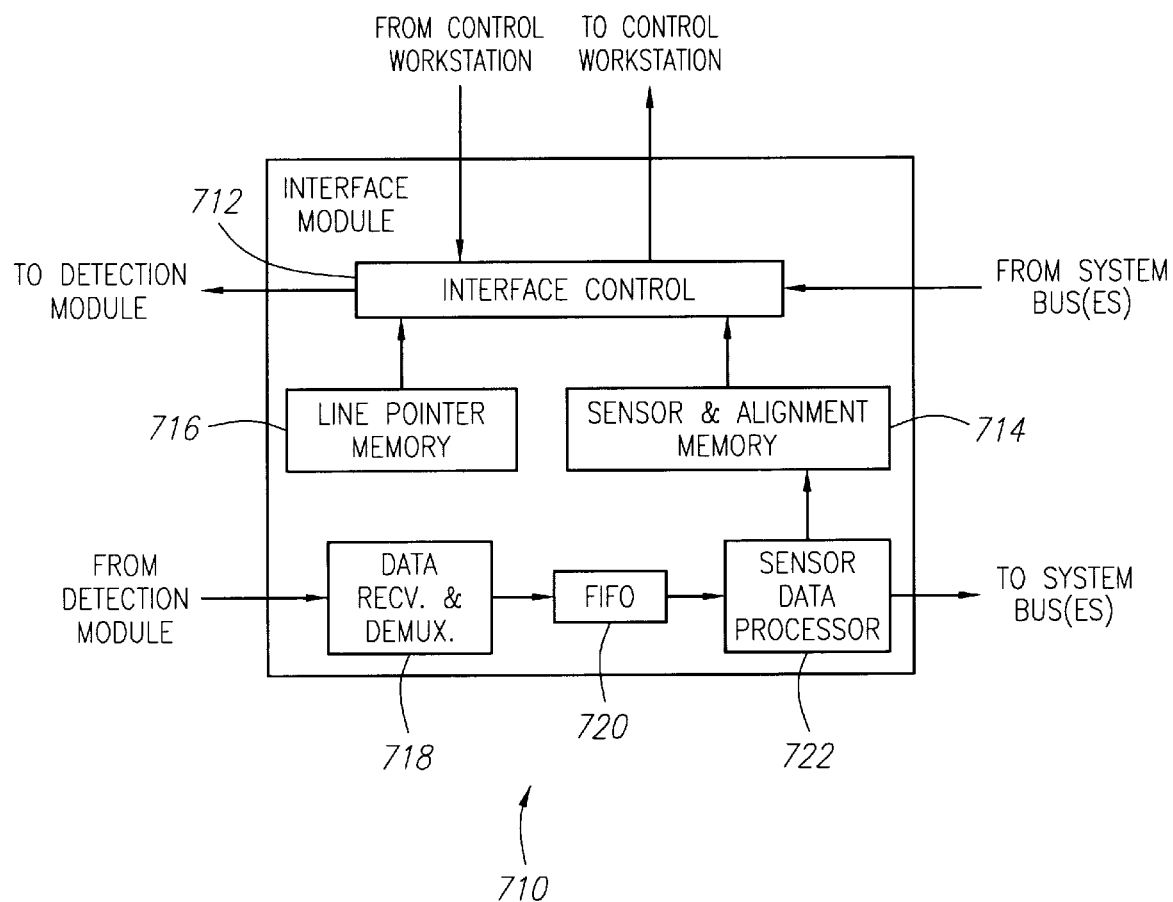
FIG. 9 is a diagram of an embodiment of an interface module.

FIG. 9 diagrams an embodiment of an interface module 710. Signals representing x-ray transmissiveness information sent from detection module 700 to interface module 710 is received and demultiplexed by data receiver 718. The x-ray transmissiveness information received by data receiver 718 is serially fed into FIFO memory 720. FIFO memory 720 regulates the transfer of data that is sent to sensor data processor 722. If the imaging system is in image acquisition mode, then signals representing x-ray transmissiveness information is passed from sensor data processor 722 to the plane reconstruction modules 730. If the imaging system is in sensor or alignment modes, then sensor data processor 722 sends x-ray transmissiveness information to a sensor and alignment memory 714. Sensor and alignment memory 714 stores information for transmission to control workstation 150 when the detection module 700 is operated in alignment or sensor mode. Line pointer memory 716 stores control information received from control workstation 150 that represents the order and stepping pattern of the electron beam and provides signals representing this information to detection module 700. Interface controller 712 receives and transmits signals between the interface module 710 and control workstation 150, and also transmits signals to the detection module 700.

Figure 10:
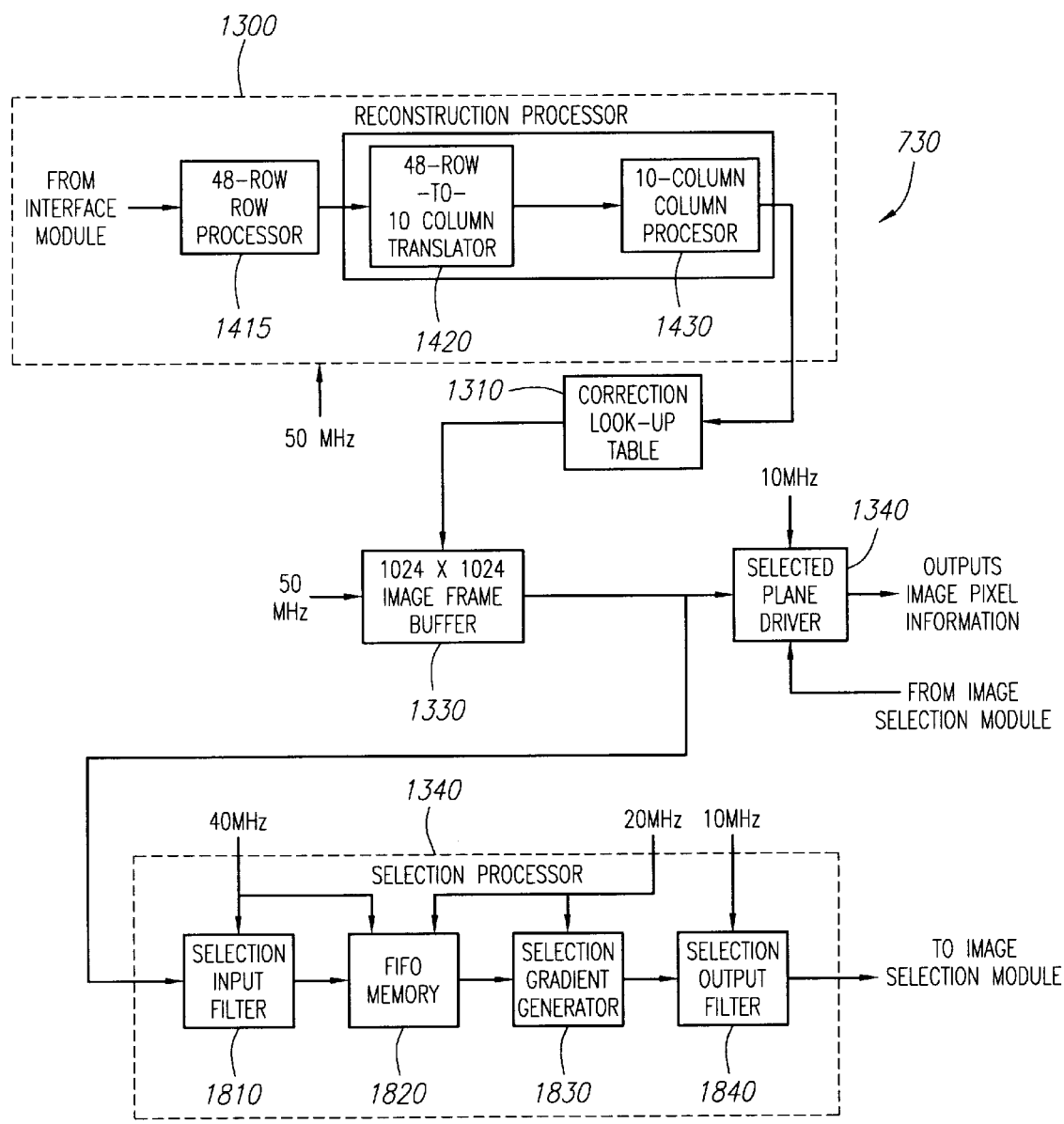
FIG. 10 is a diagram of an embodiment of an image plane reconstruction module.

FIG. 10 depicts an embodiment of a plane reconstruction module 730. Each plane reconstruction module 730 reconstructs an array of image pixels for a single plane at a particular depth between the x-ray source and detector array. The image reconstruction system 65 can employ a plurality of plane reconstruction modules 730 to reconstruct a plurality of image arrays for planes at various depths between the x-ray source and detector array. The preferred embodiment comprises 16 separate plane reconstruction modules 730 that each reconstructs an image array for a single plane. In an alternate embodiment, each plane reconstruction module comprises components to reconstruct two or more image arrays for a corresponding number of image planes. Each plane reconstruction module 730 includes a reconstruction processor 1300, a correction look-up table 1310, an image frame buffer 1330, a selection processor 1340, and a selected plane driver 1340.

Reconstruction processor 1300 includes circuitry for generating an array of image pixels representing a particular object plane according the methods described with respect to FIGS. 2–6. Reconstruction processor 1300, which preferably operates at a 50 MHz clock, processes data received from interface module 710 that correspond to x-ray transmissiveness information detected at the multi-detector array 60. In the preferred embodiment, for x-ray subpaths that are assigned to the same image pixel in an image plane are combined to generate data for a single image pixel. This process is repeated for each image pixel in the image plane. The output of the reconstruction processor 1300 is an x by y array of image pixel information for an image plane.

Signals representing the image pixel information is output from reconstruction processor 1300 to correction look-up table 1310. Correction look-up table 1310 provides correction for defects in the image pixel information. For example, such imaging defects may occur due to the process of mapping items of x-ray transmissiveness information to image pixel values, in which certain image pixels have an inaccurate value relative to other image pixels because they receive more or less x-ray transmissiveness information than the other image pixels. As another example, various manufacturing and design defects/tolerances in the components of the multi-detector array 60 may result in the generation of image information that is not entirely accurate. A particular detector element may be defectively manufactured, which always causes a resulting image pixel at coordinate (50,50) to have a value that is 5% too high. Prior to use of image reconstruction system 65, the correction look-up table 1310 is programmed with calibration setting to correct for any imaging defects. The look up table 1310 normalizes the image pixel values to correct for any image defects that appear when the system is operated without an object in the field of view. Thus, for the image array having an image pixel that is always 5% too high, the correction look-up table 1310 is programmed to reduce that incorrect image element by the appropriate amount to generate an accurate image pixel value.

The image frame buffer 1320, which preferably operates on a 50 MHz clock, stores the image pixels after normalization by the look-up table 1310. In the preferred embodiment the image buffer is a single memory, however, it may be replaced with a number of smaller memories or shift registers.

A selection processor 1340 receives the corrected image pixel information from image frame buffer 1330. Selection processor 1340 contains circuits to process the pixels in an image plane to assist in determining which of the image pixels at a particular x and y coordinate from the various image planes are chosen for display. The prior section entitled "Image Reconstruction" described several methods that are applicable to select which of the image pixels that have the same x and y coordinates but different z coordinates corresponding to different image planes are displayed. For example, one method involves calculating the gradient or slope of an image pixel with its neighboring image pixels to select display pixels for a particular portion of a display image. In the preferred embodiment, the selection processor produces a quantifiable "selection" or gradient value for each image pixel that can be compared with gradient values for pixels on other image planes to determine which will be selected for display.

The selection or gradient values for all pixels that are reconstructed in the image reconstruction system 65 are sent to an image selection module 1050 (FIG. 7). The image selection module 1050 compares the selection or gradient values that it receives to select one of the reconstructed image pixels for display. The particular plane reconstruction module 730 that reconstructs the image plane containing the selected image pixel is notified of this selection via selected plane driver 1340. The selected plane driver 1340 for that particular plane reconstruction module 730 then outputs the image information for the selected image pixel to the image processor 1060 for display.

Each reconstruction processor 1300 preferably comprises a row processor 1415, a row-to-column translator 1420, and a column processor 1430. The reconstruction processor 1300 takes x-ray transmissiveness information received by an array of detector elements for successive illuminations by an x-ray source, and converts that information to an array of image pixels. In the preferred embodiment, the x-ray source comprises a 100 by 100 array of x-ray source locations and a 48 by 48 array of detector elements. The reconstruction processor 1300 converts streams of 48 by 48 image information arrays into smaller arrays of image pixel information. In the presently preferred embodiment, for each 48 by 48 array of x-ray transmissiveness information received for a single illumination, a 10 by 10 array of image pixels is generated. This 10 by 10 array of image pixel information is generated by combining the most recent 48 by 48 array of x-ray transmissiveness information with portions of previously received 48 by 48 arrays of x-ray transmissiveness information that relate to image pixels within this 10 by 10 array of image pixels. Therefore, for a 100 by 100 array of x-ray source locations, an embodiment of the invention generates a 1000 by 1000 array of image pixels (which is (100*100 x-ray source locations)*(10*10 image pixels per source location)).

In the preferred embodiment, the row processor 1415 receives a stream of data representing 48 by 48 arrays of image information, and processes this image information to combine information from various rows that relate to the same image pixel to generate a 10 row by 48 column array of image pixel information. The row-to-column translator 1420 and column processor 1430 then takes the 10 row by 48 column output of the row processor 1415 to combine image information from various columns that relate to the same image pixel. The output of the column processor 1430 is a 10 row by 10 column array of image pixel information for a particular image plane for a particular x-ray source location or collimator aperture.

Figure 11:
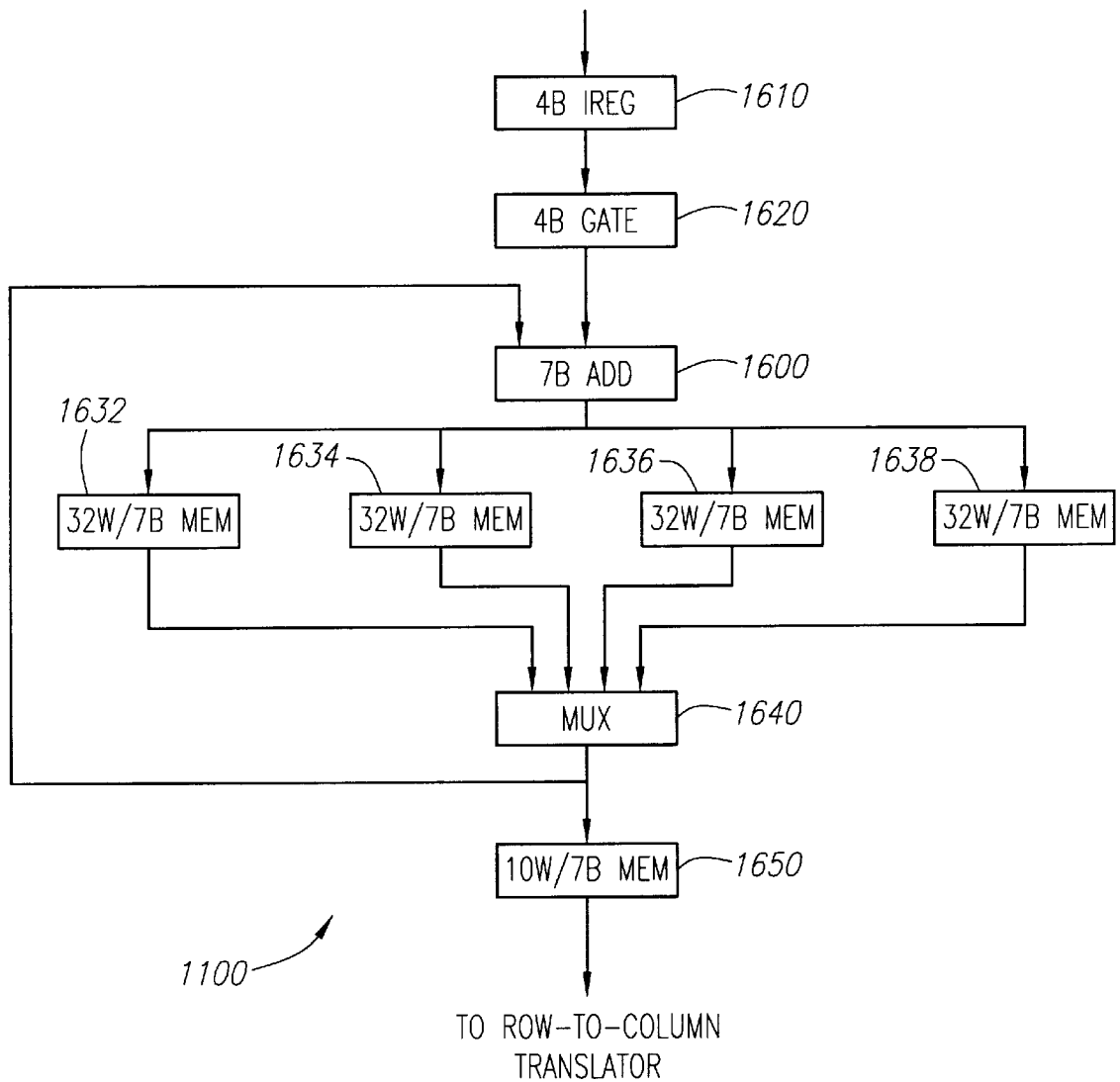
FIG. 11 is a diagram of a row processor module according to an embodiment of the present inventions.

FIG. 11 depicts an embodiment of a row processor module 1100. The embodiment described with reference to FIG. 11 processes information for a single row of detector elements. Thus, row processor 1415 comprises forty-eight (48) row processor modules 1100 to process forty eight (48) rows of information received from the multi-detector array. X-ray transmissiveness information for a row of detector elements is received through an input register 1610 and gate 1620. Image information from different detector elements that relate to the same image pixel are combined by an adder 1600. The pixel information generated by adder 1600 is fed to a row adder memory. In an embodiment, row adder memory is a 128 word memory, comprised of four separate 32 word, 7 bit memories 1632, 1634, 1636 and 1638.

If pixel information has already been received for a particular image pixel, but that pixel information is incomplete because there is further image information for that image pixel that has not yet arrived, then that incomplete pixel information is stored within memories 1632, 1634, 1636, or 1638. When new image information for that same image pixel arrives at adder 1600, then the previously stored pixel information is selectively passed through multiplexor 1640 to the adder 1600 to be combined with the new image information. If all the image information that is expected to arrive for a particular image pixel has already been processed, then the pixel information for that image pixel is passed through multiplexor 1640 to a word memory 1650. The particular memory 1632, 1634, 1636, or 1638 that stores this information can thereafter be re-used to hold pixel information for another image pixel. Word memory 1650 stores the pixel information for image pixels which will not receive any further x-ray transmissiveness information from any of the detectors in the row of detectors associated with the row processor 1100. This pixel information is then sent to the row-to-column translator 1420 and column processor 1430.

As stated above, the output of the row processor 1415 is a 10 row by 48 column array of information. This 10 by 48 array of information is processed by the row-to-column translator 1420 and column processor 1430 to generate a 10 row by 10 column array of image pixel information for a particular object plane. The image pixel information is output from row-to-column translator 1420 into the column processor 1430 such that all of the partial image pixel information in one column of row-to-column translator 1420 is output to one column processor. Preferably, the number of column processors 1430 utilized is equal to the m value of the image plane being reconstructed (as described in the Image Reconstruction section), since this allows for the most efficient processing capability in terms of speed. Column processor 1430 adds partial image pixels provided from the row processors with partial image pixels from other row processors assigned to the same image pixels to create a completed image pixel information for each image pixel that makes up the image plane.

Figure 12:
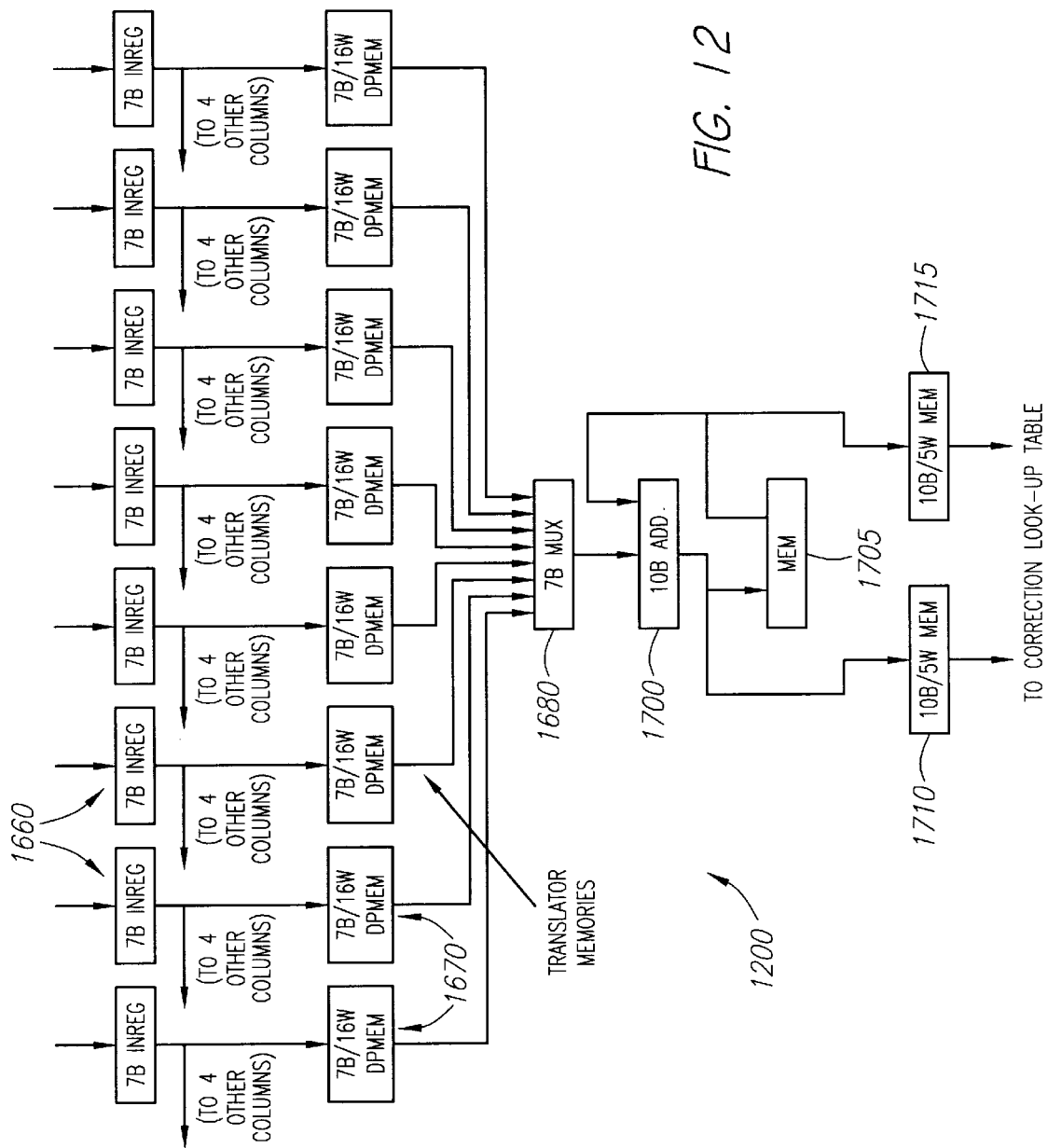
FIG. 12 is a diagram of a row-to-column translator and column processing unit according to an embodiment of the present inventions.

FIG. 12 represents an embodiment of a circuit 1200 that combines the functions of the row-to-column translator 1420 and column processor 1430. Each column input to circuit 1200 includes an input register 1660 and a memory 1670. In a preferred embodiment, each memory 1670 and input register 1660 handles image pixel information received from six row processor modules 1100. The output of each memory 1670 is output to multiplexor 1680 that outputs a signal that comprises image pixel information stored in a memory 1670. The data for a column of information is passed through multiplexor 1680 to an adder 1700. Adder 1700 combines information together that relate to the same image pixel. If the resulting pixel information for a particular image pixel is incomplete because there is further image information for that image pixel that has not yet been processed, then that incomplete pixel information is stored at a memory 1705. In an embodiment, memory 1705 comprises a register and an off-board memory. When additional image information for that same image pixel arrives at adder 1700, then the previously stored pixel information is returned to the adder 1700 to be combined with the additional information. If all the image information that is expected to arrive for a particular image pixel has already been processed, then the pixel information for that image pixel is passed to memory 1710 or 1715. This information is then delivered to the correction look-up table 1310 and a corrected set of image information for an array of image pixels is delivered to an image frame buffer 1330 (FIG. 10).

As stated above, a selection processor 1340 receives the corrected image pixel information from image frame buffer 1330. Selection processor 1340 contains circuits to process the pixels in an image plane to assist in determining which of the image pixels at a particular x and y coordinate from the various image planes are chosen for display. In the presently preferred embodiment, the selection processor quantifies the gradient value for each image pixel in the reconstructed image planes. An embodiment of a selection processor 1330 comprises a selection input filter 1810, a FIFO memory 1820, a selection gradient generator 1830, and a selection output filter 1840.

Figure 13A:
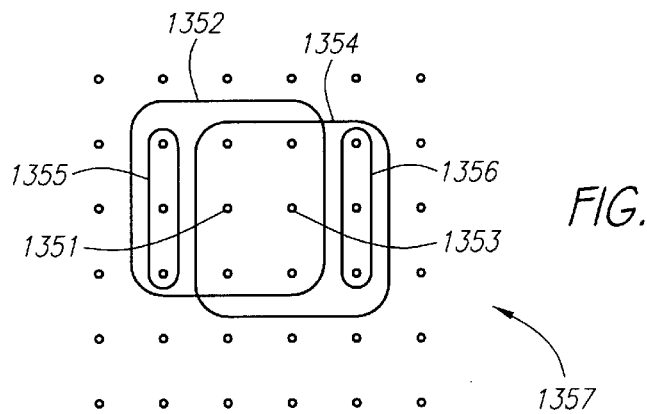
FIG. 13a illustrates selection filtering according to an embodiment of the invention.

The selection input filter 1810 functions to "smooth" data by ameliorating differences between adjacent image pixels caused by noise. The presently preferred selection input filter 1810 is a lowpass filter, such as a "boxcar" filter that takes the moving average value of a group of image pixels surrounding any image pixel. For example, an embodiment of a boxcar filter can generate a moving average based upon a shifting group of nine image pixels. To illustrate, shown in FIG. 13a is a representative group of image pixels 1357. The calculated filter value for image pixel 1351 is derived from an average of the values of the nine image pixels within box 1352. The calculated filter value for image pixel 1353 is derived from an average of values for the nine image pixels within box 1354. The filtering process is performed for the entire image plane by sequentially generating this moving average for every image pixel in the plane.

Note that if an average value has already been derived for the nine image pixels in box 1352, then it is not necessary to add all the individual values of the nine image pixels in box 1354 to derive the average of those image pixels. Instead, the average value of the nine image pixels in box 1354 can be derived by taking the already-calculated sum of the values in box 1352, then subtract the value of the three image pixels in circled column area 1355, and then adding the value of the three image pixels in circled column area 1356. It can be appreciated that this optimization can also be performed when the image pixel under examination is on the next row. Thus, for an image pixel in the next row, an average can be derived by subtracting the value of a group of three image pixels in a particular area of a previous row of image pixels, while adding the value of a group of three image pixels in a particular area of the next row.

Figure 13B:
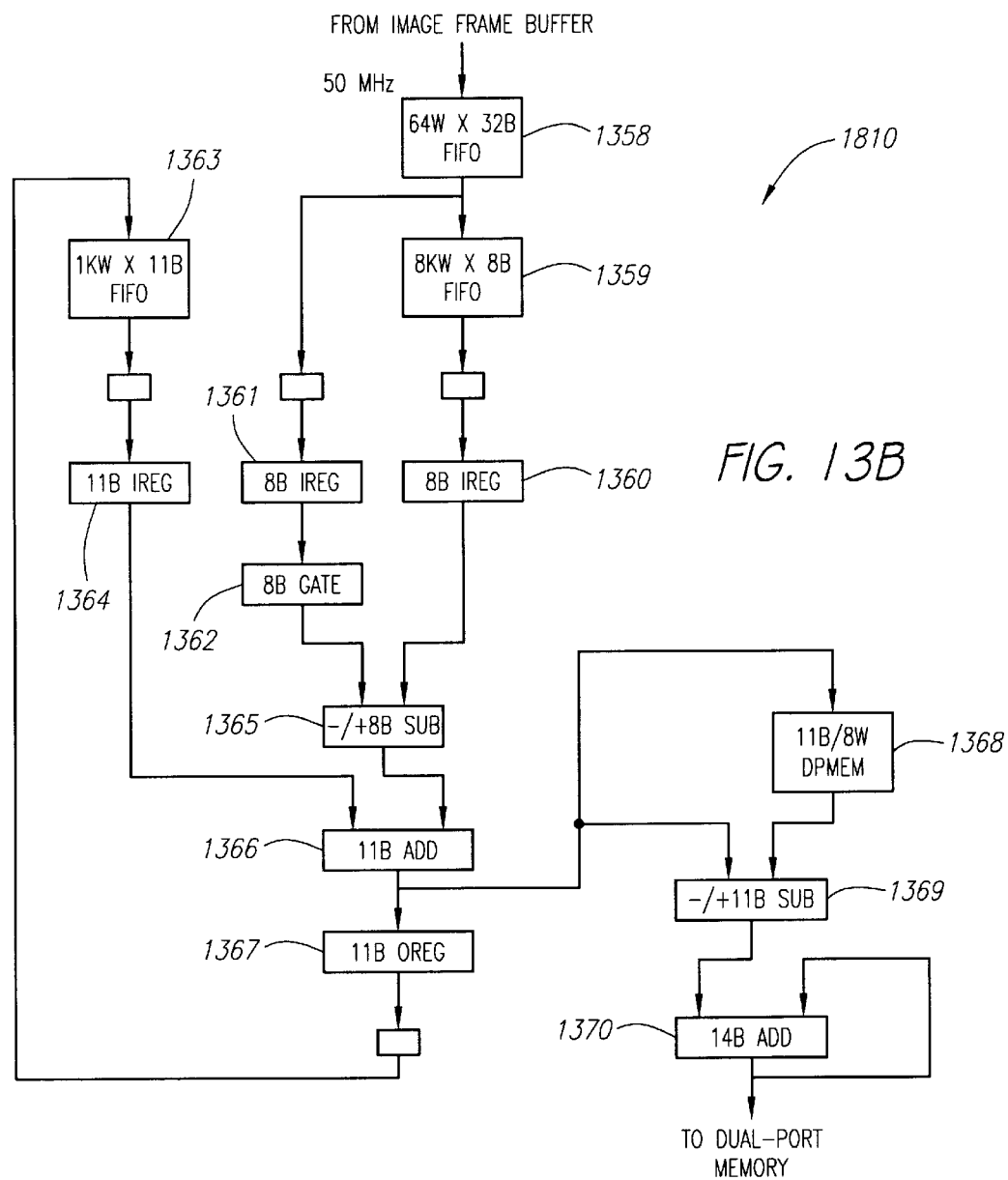
FIG. 13b is a diagram of a selection input filter according to an embodiment of the present inventions.

Shown in FIG. 13b is a diagram of an embodiment of a selection input filter 1810 that can perform this type of filtering. Image pixel information is received though a FIFO 1358. Image pixel information from a prior area of an image pixel column had been stored in FIFO 1359. When the new information arrives through FIFO 1358, it is sent through a register 1361 and gate 1362 to a subtractor 1365. The previously stored image pixel information stored in FIFO 1359 is sent through a resister 1360 to the subtractor 1365, where it is subtracted from the new image pixel information. The output of the subtractor 1365 is sent to an adder 1366, where it is added to previously processed information for an area of an image pixel array that had been stored in FIFO 1363. The output of adder 366 is sent to FIFO 1363, where it awaits farther addition to other pieces of information. In addition, the output of adder 1366 is sent to a subtractor 1369, where it subtracts a stored value from memory 1368 corresponding to a prior area of an image pixel row. The output of the subtractor 1369 is fed to an adder 1370, where it is added to a value that corresponds to an area of an image pixel.

The filtered image pixel values are sent to a FIFO memory 1820 (FIG. 10). FIFO memory 1820 controls the flow of data between selection input filter 1810 and the selection gradient generator 1830. Selection gradient generator 1830 performs computations to produce a quantifiable selection or gradient value that represents whether a particular image pixel at an x and y coordinate in an image array should be selected as the display pixel at that coordinate on a display image. In the preferred embodiment, this quantifiable selection value is generated by determining the gradient (e.g., the variation) for each image pixel with respect to its neighboring image pixels. In an embodiment, the gradient is determined by taking the absolute value of the difference of each image pixel and the image pixel that are above, below, on the right and on the left of that image pixel. However, other methods of gradient determination may be used in accordance with present invention without departing from the scope and spirit of the present invention. For instance, it is possible to determine the square root of the sum of the squared differences between each image pixel and adjacent or other neighboring image pixels.

Figure 14A:
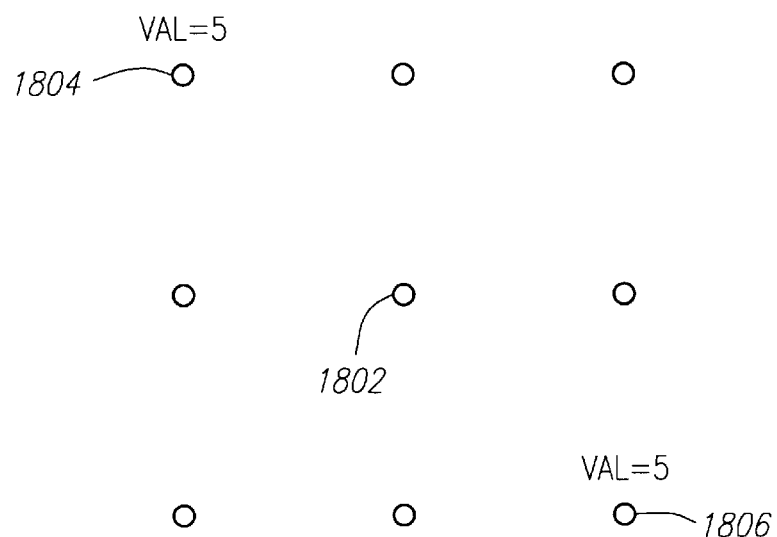
FIGS. 14a and 14b illustrates selection gradient processing according to an embodiment of the invention.

FIG. 14a illustrates a process for gradient determination according to an embodiment of the invention. Shown in FIG. 14a is a portion of an image pixel array on a first image plane. As stated above, the gradient determination for an image pixel can be performed by taking the absolute value of the difference between the values of two opposing image pixel neighbors. Thus, the gradient determination for image pixel 1802 includes calculating the absolute value of the difference between the value of its neighboring image pixels 1804 (val=5) and 1806 (val=5). Since the absolute value of (5—5) is 0, image pixel 1802 is represented by a low gradient value. In other words, since the absolute difference value for the neighboring image pixels of image pixel 1802 is low, the level of "detail" to be shown by this image pixel is also low. Therefore, the gradient value that has been derived for this image pixel indicates that it is not likely to be selected for display. For the sake of clarity and explanation, the difference between only two neighboring image pixels is illustrated here; however, as stated above, additional methods can be employed to determine the gradient value, including performing the absolute difference calculations for many more neighboring image pixels.

Figure 14B:
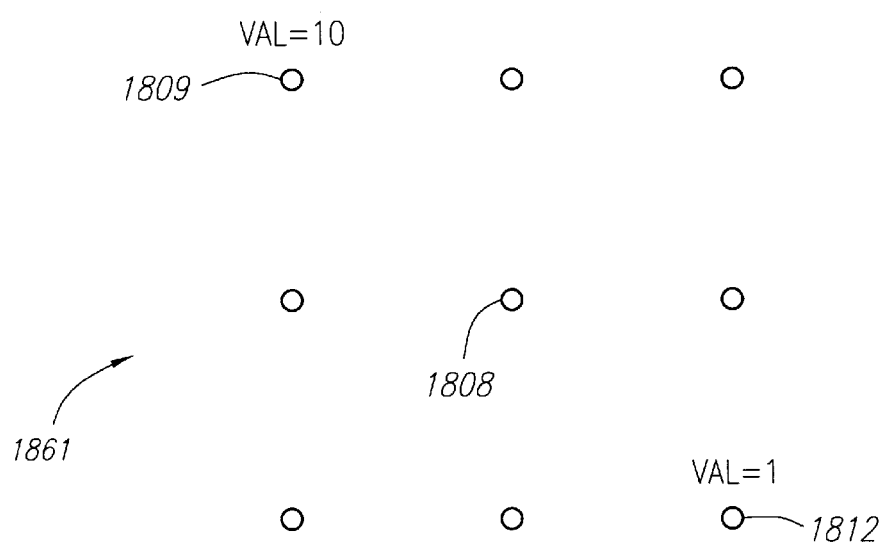

FIG. 14b depicts the same image pixel coordinates as shown in FIG. 14a, but is located on a second image plane. Thus, image pixel 1808 in FIG. 14b has the same x and y coordinates as image pixel 1802 in FIG. 14a. The gradient value derived for image pixel 1808 is the absolute difference of the values of its neighbor pixels 1809 (val=10) and 1812 (val=1). Since the absolute value of the difference between these two neighbor pixels is 9 (abs(10-1)), the gradient value for image pixel 1808 is relatively high. Thus, this determination indicates that image pixel 1808 has a higher gradient value (and therefore shows more detail) than image pixel 1802, and is more likely to be selected as the image pixel to be displayed at their corresponding x,y coordinates on the display image.

Figure 14C:
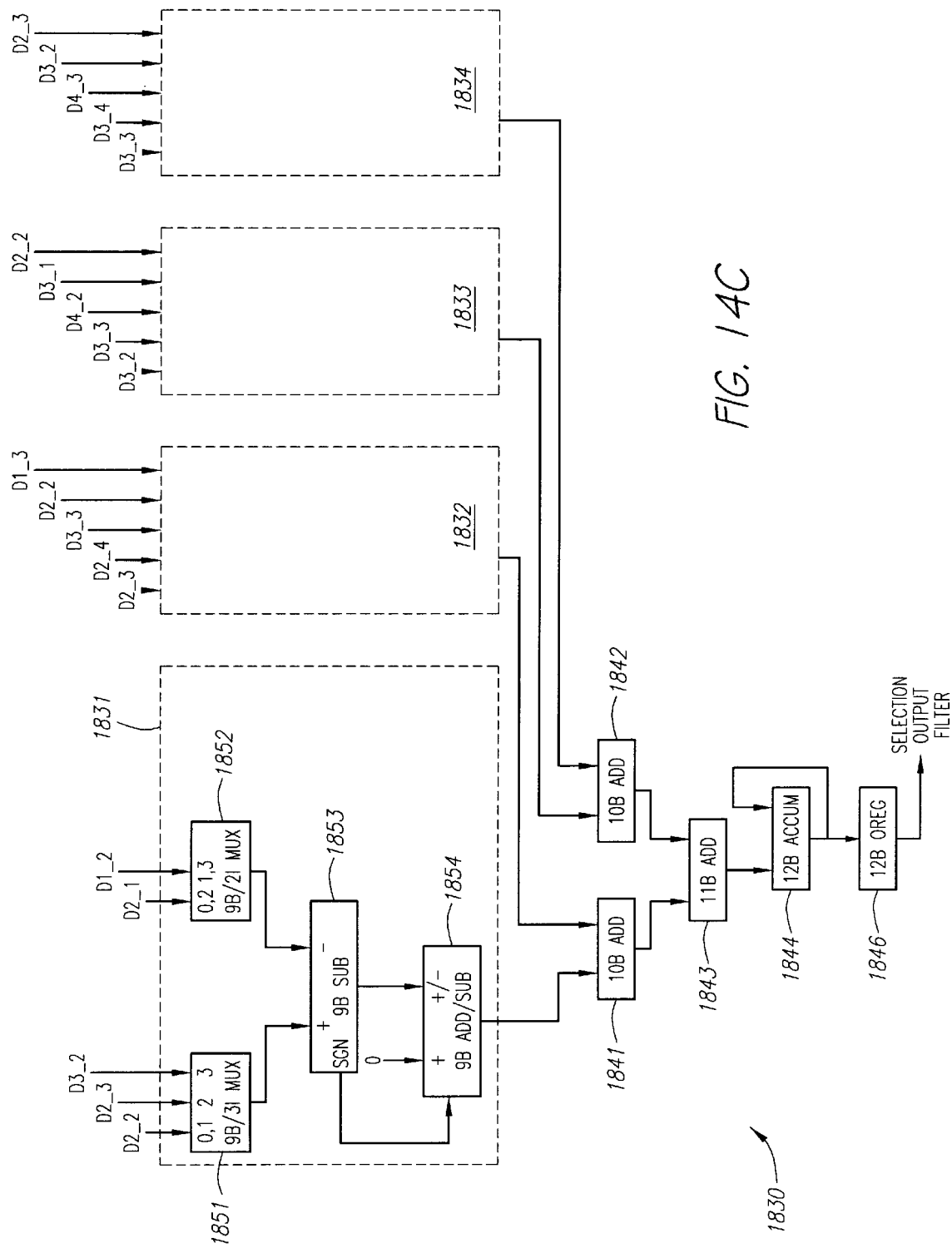
FIG. 14c is a diaorarfa selection gradient processor according to an embodiment of the present inventions.

FIG. 14c diagrams an embodiment of a selection gradient generator 1830. In FIG. 14c, selection gradient generator 1830 comprises four gradient processors 1831, 1832, 1833, and 1834. Each gradient processor calculates the gradient value for an image pixel. In the present embodiment, the gradient values for a group of four image pixels are averaged together (by adders 1841, 1842, 1843 and accumulator 1844) to produce a group gradient value. The group gradient value allows each group of four image pixels in an image plane to be considered for display together as a group, rather than individually on a pixel-by-pixel basis. This can help prevent harshness in the display image when unrelated (and possibly mismatched) image pixels are individually selected and displayed in the display image. Alternatively, selection gradient generator 1830 can generate individual gradient values for each image pixel, so that each image pixel can be individually judged for its appropriateness for display.

Gradient processor 1831 includes multiplexors 1851 and 1852 to receive image pixel values for neighboring image pixels along opposing sides of the image pixel for which a gradient value is being calculated. Subtractor 1853 performs the differencing calculation between the image pixel values of the neighboring image pixels. The absolute value of the difference is calculated by ADD/SUB unit 1854, and the final gradient value for the image pixel is then output to the adder 1841. Gradient processors 1832, 1833, and 1834 include a similar set of structures.

The gradient information is then provided through register 1846 to a selection output filter 1840 (FIG. 10), which preferably performs the same functions that are performed by the selection input filter 1810. That is, selection output filter 1840 takes the average value for a group of gradient information corresponding to a group of image pixels around a specific gradient value and substitutes the average value for the gradient information for each image pixel. Thus, in the preferred embodiment, selection output filter 1840 comprises the circuits and performs the functions that are described in more detail with respect to selection input filter 1810 (FIGS. 13a and 13b).

Figure 15:
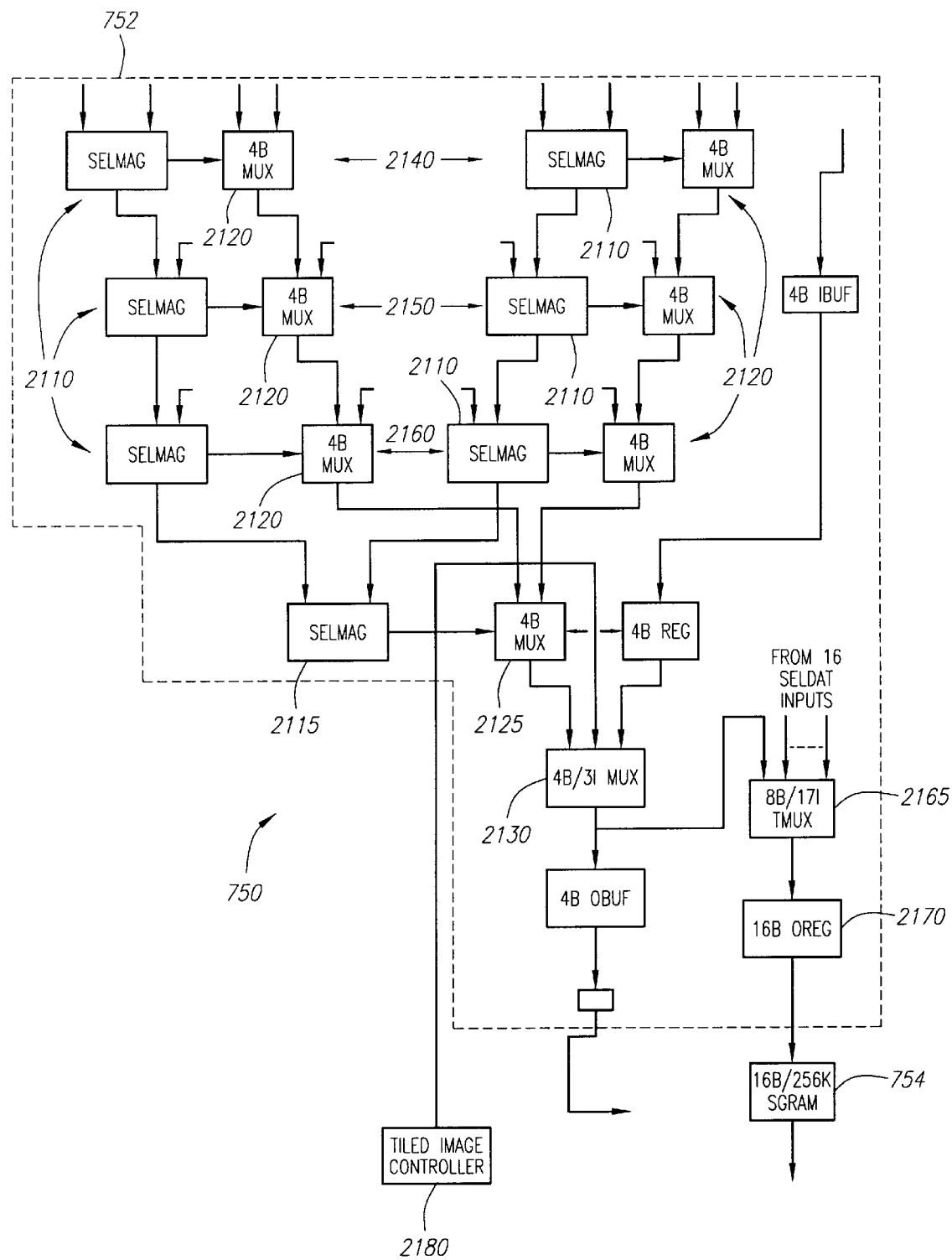
FIG. 15 is a diagram an embodiment of an image selection module.

Referring to FIG. 15, an image selection module 750 receives signals representing gradient values from the selection output filter 1840. The gradient values that are input into image selection module 750 during each cycle correspond to image pixels that have the same x and y coordinates but are located on different image planes. The gradient values are input into one or more selection magnitude circuits 2110. Each of the selection magnitude circuits 2110 compares two gradient values. The selection magnitude circuit 2110 selects the gradient value that is the greater of the two gradient values inputs. Each magnitude selection circuit 2110 has associated with it a selection multiplexor 2120. Selection multiplexor 2120 contains information indicating the plane reconstruction module 730 from which each of the image pixels or gradient values was produced.

In operation, each selection magnitude circuit 2110, except for the last magnitude selection circuit 2115 located at the lowest position in image selection module 750, outputs the selected gradient value to a selection magnitude circuit 2110 below it. Each selection magnitude circuit 2110 also provides a signal to its corresponding selection multiplexor 2120 instructing the selection multiplexor 2120 to output the plane location information indicative of the image plane reconstruction module 730 from which the image pixel or gradient value was selected. The plane location information is output to either a selection multiplexor 2120 associated with the selection magnitude circuit 2110 below the current one or to the output multiplexor 2130 in the case of the last selection multiplexor 2125.

The presently preferred plane selector 752 includes four rows of magnitude selection circuits 2110. The first row 2140 preferably includes a number of magnitude selection circuits 2110 equal to half the number of image plane reconstruction modules 730. Thus, if the number of image plane reconstruction modules is sixteen then there are preferably eight magnitude selection circuits in the first row 2140. The second row 2150 preferably includes half the number of magnitude selection circuits as the first row 2140 and third row 2160 preferably includes half the number of magnitude selection circuits 2110 as second row 2150. The last selection magnitude circuit 2115 outputs the highest magnitude gradient values for the image pixels that have the same x,y coordinates but are located on different image planes. The last selection magnitude circuit 2115 therefore determines which specific image pixel is selected for display or processing.

The above-described structure is efficient in that it compares two image pixels and then discards the one that cannot be selected. Therefore, the ones that cannot be selected is automatically discarded without doing additional comparisons or using a large matrix to perform calculations. This improves the processing speed of the imaging system and reduces the number of components utilized to perform processing. Plane select image buffer 754 receives the plane location of the selected image pixel through a multiplexor 2165 and output register 2170. Tiled image controller 2180 allows the display of pieces of each image. The tiled image controller allows the user to select for display or processing specific image pixels without regard to the image plane or location. For example, a user can select two or more image pixels that have the same x, y coordinates but are located on different image planes.

Figure 8:
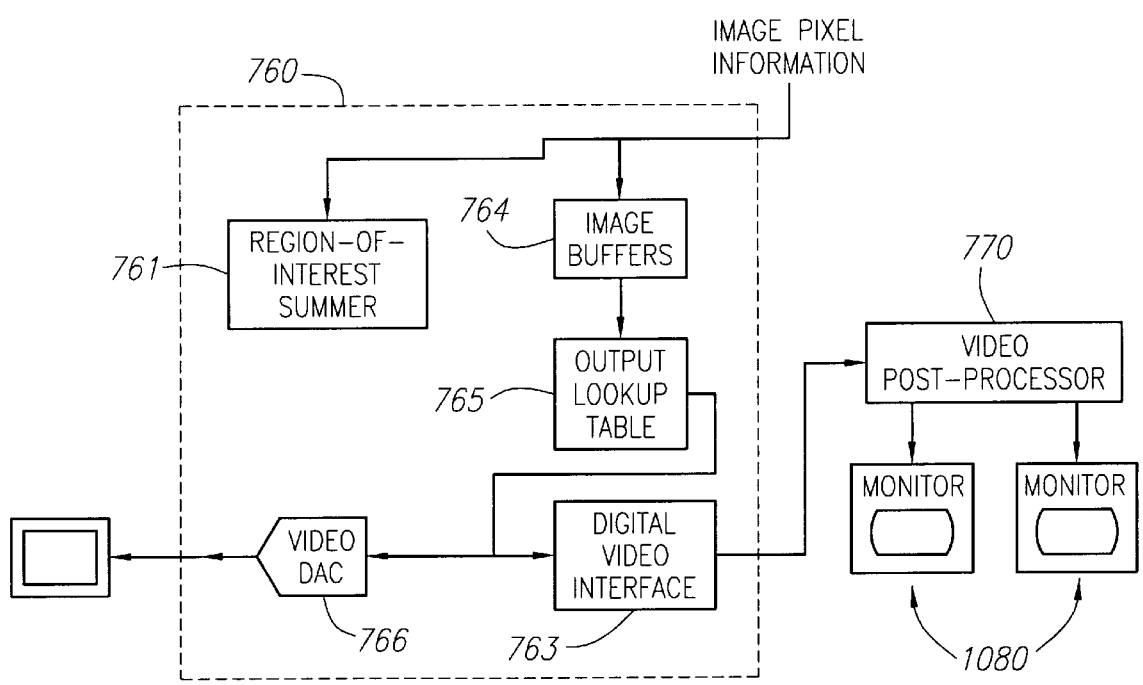
FIG. 8 is a diagram of an image preprocessor according to an embodiment of the present inventions.

Referring to FIG. 8, the signals representing image pixel information for image pixels selected for display is sent to an image processor 760. Image preprocessor 760 contains circuitry for calibrating brightness of the display by determining the magnitude of the image pixels in various regions with region-of-interest summer 761. Region-of-interest summer 761 combines image pixels located in the same area of a display plane selected for display. The output of region-of-interest summer 761 can be used to determine whether to alter the intensity of the electron beam in the source to adjust x-ray intensity of the system. The output of the region-of-interest summer 761 is also provided to digital video interface 763 for output to video post processor 770 for calibration of the brightness of a display monitor 1080. The preprocessor image buffers 764 provide information to preprocessor look-up table 765 that performs gamma correction functions on the image pixels selected for display. The corrected image pixels can be provided to a digital-to-analog converter 766 for use in an analog display.

Digital video interface 767 supplies the processed image pixels from the image preprocessor 760 to the video post processor 770. The information output from image preprocessor 760 is output to video post processor 770 that operates the display 1080, which are preferably standard video monitors. Video post processor 770 also preferably contains circuitry for storing the outputted image pixels for storage to be replayed or used for other computations.

While the embodiments, applications and advantages of the present invention have been depicted and described, there are many more embodiments, applications and advantages possible without deviating from the spirit of the inventive concepts described herein. Thus, the inventions are not to be restricted to the preferred embodiments, specification or drawings. The protection to be afforded this patent should therefore only be restricted in accordance with the spirit and intended scope of the following claims.

What is claimed is:

1. An image reconstruction system comprising:

a reconstruction processor comprising a reconstruction processor input and a reconstruction processor output, said reconstruction processor input configured to receive x-ray transmissiveness information, said reconstruction processor output configured to output image pixel information corresponding to x-ray transmissiveness information for positions at particular depths within of said object;

a selection processor at which image data corresponding to a plurality of depths within said object are selected;

a display device having a display image comprising said image data; and a correction look up table comprising data to correct said image data.

2. An image reconstruction system comprising:

a reconstruction processor comprising a reconstruction processor input and a reconstruction processor output, said reconstruction processor input configured to receive x-ray transmissiveness information, said reconstruction processor output configured to output image pixel information corresponding to x-ray transmissiveness information for positions at particular depths within of said object;

a selection processor at which image data corresponding to a plurality of depths within said object are selected; and a display device having a display image comprising said image data;

wherein said reconstruction processor comprises:

a plurality of row processors each comprising a row processor input and a row processor output, said row processor input receiving said information corresponding to a row of positions in said object and said row processor output providing partial image pixel information; and a plurality of column units each comprising an column unit input and a column unit output, said column unit input receiving said partial image pixel information and said column unit output providing said image pixel information.

3. The image reconstruction system of claim 2 wherein each column unit comprises a row to column translator comprising a translator input and a translator output, said translator input receiving said partial image pixel information and a column processor comprising a column processor input and a column processor output, said column processor input coupled to said translator output and said column processor output providing said image pixel information.

4. An image reconstruction system comprising:
- a reconstruction processor comprising a reconstruction processor input and a reconstruction processor output, said reconstruction processor input configured to receive x-ray transmissiveness information, said reconstruction processor output configured to output image pixel information corresponding to x-ray transmissiveness information for positions at particular depths within of said object;
- a selection processor at which image data corresponding to a plurality of depths within said object are selected; and
- a display device having a display image comprising said image data;
- wherein said selection processor comprises a gradient generator that generates a gradient value for neighboring image pixels.

5. The image reconstruction system of claim 4 wherein said selection processor further comprises a selection input filter and a selection output filter.

6. An image reconstruction system comprising:
- a reconstruction processor comprising a reconstruction processor input and a reconstruction processor output, said reconstruction processor input configured to receive x-ray transmissiveness information, said reconstruction processor output configured to output image pixel information corresponding to x-ray transmissiveness information for positions of said object;
- a selection processor at which image data corresponding to said object are selected, wherein the selection processor does not select the image data based upon a planar relationship of the selected image data; and
- a display device having a display image comprising said image data.

7. The image reconstruction system of claim 6 further comprising a scanning beam x-ray imaging system, said scanning beam x-ray imaging system generating said x-ray transmissiveness information.

8. The image reconstruction system of claim 6 further comprising a computed tomography imaging system, said computed tomography imaging system generating said x-ray transmissiveness information.

9. An image reconstruction system comprising:
- one or more first signals comprising x-ray transmissiveness information for an object;
- one or more second signals comprising pixel information for a plurality of depths within said object, said pixel information comprising selected combinations of said x-ray transmissiveness information; and
- one or more third signals comprising a display image, said display image comprising selected data from said pixel information, said selected data from said pixel information corresponding to image pixels at varying depths within said object;
- wherein said one or more third signals are generated based upon the gradient between neighboring image pixels.

10. An image reconstruction system comprising:
- a first processor at which image pixel information for a plurality of depths within an object to be imaged is generated;
- a second processor at which particular image pixel information for display corresponding to various depths within said object from said image pixel information are selected; and
- a display device having a display image comprising said particular image pixel information;
- wherein said first processor comprises:
  - one or more row processors, said one or more row processors receiving information corresponding to a row of positions of a plurality of positions in said object and generating partial image pixel information; and
  - one or more column units, said one or more column units receiving said partial image pixel information from said one or more row processors and generating said image pixel information.

11. An image reconstruction system comprising:
- a first processor at which image pixel information for a plurality of depths within an object to be imaged is generated;
- a second processor at which particular image pixel information for display corresponding to various depths within said object from said image pixel information are selected; and
- a display device having a display image comprising said particular image pixel information;
- wherein said first processor further comprises a selection processor, said selection processor receiving said image pixel information and outputting pixel selection information.

12. The image reconstruction system of claim 11 wherein said selection processor comprises a gradient generator.

13. The image reconstruction system of claim 11 wherein said selection processor comprises a selection input filter and a selection output filter.

14. An image reconstruction system comprising:
- a first processor at which image pixel information for an object to be imaged is generated;
- a second processor at which particular image pixel information for display corresponding to said object from said image pixel information are selected, wherein the second processor does not select the particular image pixel information based upon a planar relationship of the selected particular image pixel information; and
- a display device having a display image comprising said particular image pixel information.

15. The image reconstruction system of claim 14 further comprising a computed tomography imaging system, said computed tomography imaging system generating x-ray transmissiveness information, said first processor receiving said x-ray transmissiveness information.

16. The image reconstruction system of claim 14 further comprising a scanning beam x-ray imaging system, said scanning beam x-ray imaging system generating x-ray transmissiveness information, said first processor receiving said x-ray transmissiveness information.

17. An image reconstruction system comprising:
- one or more first signals comprising x-ray transmissiveness information for an object;

one or more second signals comprising pixel information for a plurality of depths within said object, said pixel information comprising selected combinations of said x-ray transmissiveness information; and one or more third signals comprising a display image, said display image comprising selected data from said pixel information, said selected data from said pixel information corresponding to image pixels at varying depths within said object, and said selected data from said pixel information need not have a planar relationship within said pixel information.

18. The image reconstruction system of claim 17 in which said pixel information comprises information for arrays of image pixels for a plurality of image planes.

19. The image reconstruction system of claim 17 in which said pixel information comprises information for arrays of image voxels for a plurality of image slices.

20. The image reconstruction system of claim 17 in which said one or more first signals is generated by an x-ray detector.

21. The image reconstruction system of claim 17 in which said one or more third signals are generated based upon the maximum intensity of image pixels.

22. The image reconstruction system of claim 17 in which said one or more third signals are generated based upon the minimum intensity of image pixels.

23. The image reconstruction system of claim 17 in which said one or more third signals are generated based upon the contrast between neighboring image pixels.

* * * * *